(12) United States Patent
Kindler et al.

(10) Patent No.: US 9,623,000 B2
(45) Date of Patent: Apr. 18, 2017

(54) COMPOSITIONS AND METHODS FOR TREATING INFLAMMATORY DISORDERS

(75) Inventors: Seth Kindler, Tel Aviv (IL); Ascher Shmulewitz, Tel Aviv (IL)

(73) Assignee: DEKEL PHARMACEUTICALS LTD, Bnei-Brak (IL)

( * ) Notice: Subject to any disclaimer, the term of this patent is extended or adjusted under 35 U.S.C. 154(b) by 160 days.

(21) Appl. No.: 13/056,872

(22) PCT Filed: Jul. 29, 2009

(86) PCT No.: PCT/IL2009/000739
§ 371 (c)(1),
(2), (4) Date: Apr. 28, 2011

(87) PCT Pub. No.: WO2010/013240
PCT Pub. Date: Feb. 4, 2010

(65) Prior Publication Data
US 2011/0195096 A1   Aug. 11, 2011

Related U.S. Application Data

(60) Provisional application No. 61/085,008, filed on Jul. 31, 2008, provisional application No. 61/098,802, filed on Sep. 22, 2008.

(51) Int. Cl.
*A61K 31/20* (2006.01)
*A61K 31/573* (2006.01)
*A61K 45/06* (2006.01)
*A61L 27/54* (2006.01)
*A61L 31/16* (2006.01)

(52) U.S. Cl.
CPC ............ *A61K 31/20* (2013.01); *A61K 31/573* (2013.01); *A61K 45/06* (2013.01); *A61L 27/54* (2013.01); *A61L 31/16* (2013.01); *A61L 2300/222* (2013.01); *A61L 2300/41* (2013.01)

(58) Field of Classification Search
None
See application file for complete search history.

(56) References Cited

U.S. PATENT DOCUMENTS

| 2,554,736 A | 5/1951 | Haefliger et al. |
| 3,420,851 A | 1/1969 | Bloom et al. |
| 3,438,981 A | 4/1969 | Stach et al. |
| 3,505,321 A | 4/1970 | Schutz et al. |
| 3,534,041 A | 10/1970 | Van Der Burg et al. |
| 3,934,013 A | 1/1976 | Poulsen |

(Continued)

FOREIGN PATENT DOCUMENTS

| EP | 0550006 A2 | 7/1993 |
| EP | 1452179 A1 | 9/2004 |

(Continued)

OTHER PUBLICATIONS

International Preliminary Report on Patentability, WIPO (Feb. 1, 2011), 6 pages.*

(Continued)

*Primary Examiner* — Brian-Yong Kwon
*Assistant Examiner* — Kyung Sook Chang
(74) *Attorney, Agent, or Firm* — Vorys, Sater, Seymour & Pease LLP

(57) ABSTRACT

Compositions which include a corticosteroid in combination with an additional compound active in treatment of an inflammatory disorder are provided.

7 Claims, 3 Drawing Sheets

(56) References Cited

U.S. PATENT DOCUMENTS

| | | |
|---|---|---|
| 4,013,639 A | 3/1977 | Kitamura et al. |
| 4,105,785 A | 8/1978 | Mauvernay et al. |
| 4,929,637 A | 5/1990 | Baldwin et al. |
| 5,006,560 A | 4/1991 | Kreutner et al. |
| 5,059,613 A | 10/1991 | Pierce, Jr. |
| 5,242,937 A | 9/1993 | Pierce, Jr. |
| 5,248,678 A | 9/1993 | Costa et al. |
| 5,276,025 A | 1/1994 | Baldwin et al. |
| 5,464,831 A | 11/1995 | Dean et al. |
| 5,473,067 A | 12/1995 | Dean et al. |
| 5,506,224 A | 4/1996 | della Valle et al. |
| 5,508,311 A | 4/1996 | Yu et al. |
| 5,596,106 A | 1/1997 | Cullinan et al. |
| 5,646,142 A | 7/1997 | Dantanarayana et al. |
| 5,747,524 A | 5/1998 | Cullinan et al. |
| 5,792,799 A | 8/1998 | Sherman-Gold |
| 5,846,979 A | 12/1998 | Hamilton et al. |
| 6,017,919 A | 1/2000 | Inaba et al. |
| 6,054,452 A | 4/2000 | Hamilton et al. |
| 6,077,839 A | 6/2000 | WoldeMussie et al. |
| 6,331,537 B1 | 12/2001 | Hamilton et al. |
| 6,368,814 B1 | 4/2002 | Ghoshal et al. |
| 6,432,984 B1 | 8/2002 | Barth et al. |
| 6,472,423 B1 | 10/2002 | Ross et al. |
| 6,486,151 B2 | 11/2002 | Hamilton et al. |
| 6,509,367 B1 | 1/2003 | Martin et al. |
| 6,569,470 B2 | 5/2003 | Williams et al. |
| 6,645,985 B2 | 11/2003 | Barth et al. |
| 6,656,972 B2 | 12/2003 | Calignano et al. |
| 6,720,348 B2 | 4/2004 | Mylari |
| 6,821,985 B2 | 11/2004 | Chenard et al. |
| 6,897,206 B2* | 5/2005 | Sackeyfio et al. ............ 514/171 |
| 7,030,250 B2 | 4/2006 | Losada et al. |
| 7,109,353 B2 | 9/2006 | Gurjar et al. |
| 7,153,883 B2 | 12/2006 | Hamilton et al. |
| 7,169,942 B2 | 1/2007 | Moore, II et al. |
| 7,335,371 B2 | 2/2008 | Sackeyfio et al. |
| 7,348,338 B2 | 3/2008 | Arnold et al. |
| 7,544,714 B2 | 6/2009 | Burstein et al. |
| 2001/0034362 A1 | 10/2001 | Ross et al. |
| 2002/0173550 A1 | 11/2002 | Calignano et al. |
| 2002/0198250 A1 | 12/2002 | Steiner et al. |
| 2003/0049220 A1* | 3/2003 | Bailey ...................... A61K 8/34 424/70.1 |
| 2003/0186961 A1 | 10/2003 | Hamilton et al. |
| 2004/0106975 A1 | 6/2004 | Solovay et al. |
| 2004/0224876 A1 | 11/2004 | Jost-Price et al. |
| 2005/0032747 A1* | 2/2005 | Bartolini .............. C07D 209/28 514/80 |
| 2005/0054730 A1 | 3/2005 | Fu et al. |
| 2007/0110685 A1 | 5/2007 | Auspitz et al. |
| 2007/0203209 A1* | 8/2007 | Bartolini et al. ............ 514/367 |
| 2009/0118503 A1* | 5/2009 | Sprott .................. C07D 209/18 544/143 |
| 2009/0123504 A1* | 5/2009 | Feldkamp ............ A61K 9/0014 424/402 |

FOREIGN PATENT DOCUMENTS

| | | |
|---|---|---|
| EP | 1645270 A2 | 4/2006 |
| WO | 9412466 A1 | 6/1994 |
| WO | 9520393 A1 | 8/1995 |
| WO | WO02089770 A2 * | 11/2002 |
| WO | 2005099720 A2 | 10/2005 |
| WO | 2007067036 A2 | 6/2007 |
| WO | 2007071313 A2 | 6/2007 |
| WO | 2009133574 A1 | 11/2009 |

OTHER PUBLICATIONS

WO2002089770A2 (claim—english machine translation) (2002).*
WO2002089770A2 (description—english machine translation) (2002).*

Kuehl et al., (1957) The identification of N-2 (hydroxyethyl)-palmitamide as a naturally occurring anti-inflammatory agent. J Am Chem Soc 79: pp. 5577-5578.
O. Abdel-Salam, et al.; "Studies on the anti-inflammatory effect of floxetine in the rat" Pharmacological Research vol. 49; 2004; pp. 119-131.
H. Adalsteinsson, et al.; "Generation and Evaluation of Putative Neuroregenerative Drugs. Part 2—Screening Virtual Libraries of Novel Polyketides which Possess the Binding Domain of Rapamycin" Bioorganic & Medicinal Chemistry vol. 8; 2000; pp. 625-635.
A. Bella, et al.; "FK1706 Enhances the Recovery of Erectile Function Following Bilateral Cavernous Nerve Crush Injury in the Rat"; J Sex Med vol. 4; 2007; pp. 341-347.
A. Bella, et al.; "Emerging Neuromodulatory molecules for the treatment of neurugenic erectile dysfunction caused by cavernous nerve injury"; Asian Journal of Andrology vol. 10 Chapter 1; 2008; Shanghai Institute of Materia Medica, Chinese Academy of Sciences; pp. 54-59.
A. Brown; "Novel Cannabinoid Receptors"; British Journal of Pharmacology vol. 152; published Online Oct. 2007; pp. 567-575.
B. Gold; "FK506 and the Role of Immunophilins in Nerve Regeneration"; Molecular Neurobiology vol. 15; 1997; pp. 285-306.
B. Gold; "Neuroimmunophilin ligands—evaluation of their therapeutic potential for the treatment of neurological disorders"; Expert Opinion on Investigational Drugs vol. 9; 2000; pp. 2331-2342.
B. Gold, eet al.; "A Nonimmunosuppressant FKBP-12 Ligand Increases Nerve Regeneration"; Experimental Neurology vol. 147, Article No. EN976630; 1997; pp. 269-278.
X. Guo, et al.; "Neuroimmunophilin ligands exert neuroregeneration and neoroprotection in midbrain dopaminergic neurons"; European Journal of Neuroscience, vol. 13; 2001; pp. 1683-1693.
A. Heiman, et al.; "New steroidal anti-inflammatory antedrugs"; Steroids, Elsevier Science Inc., vol. 62; 1997; pp. 491-499.
K. Jonsson, et al.; "Effects of homologues and analogues of palmitoylethanolamide upon the inactivation of the endocannabinoid anandamide"; British Journal of Pharmacology, vol. 133; Nature Publishing Group; 2001; pp. 1263-1275.
D. Long; et al.; "Incorporation of Q Into the Cell Constituents of Pseudomonas and E coli—Communicaions to the Editor"; vol. 79, Oct. 1957; pp. 5577-5578.
J. Kuzmiski; "Topiramate Inhibits the Initiation of Plateau Potentials in CA1 Neurons by Depressings R-type Calcium Channels"; Epilepsia vol. 46, Chapter 4; Blackwell Publishing, Inc.; International League Against Epilepsy; 2005; pp. 481-489.
D. Lambert, et al.; "Analogues and homologues of N-palmitoylethanolamide a putative endogenous CB2 cannabinoid as potential ligands for the cannabinoid"; Biochemica et Biophysica Acta vol. 1440; 1999; pp. 266-274.
D. Lambert, et al.; "The Palmitoylethanolamide Family A New Class of Anti-Inflammatory Agents"; Current Medicinal Chemistry vol. 9; Bentham science Publishers Ltd; 2002; pp. 663-674.
M. Namazi; "Cannabinoids loratadine and allopurinol as novel aditions to the antipsoriatic ammunition"; European Academy of Dermatology and Venereology; JEADV vol. 19; 2005; pp. 319-322.
"Hydrocotarnine" XP-002651747; vol. 4809; p. 855.
G. Re, et al.; "Palmitoylethanolamide endocannabinoids and related cannabimimetic compounds in protection agains tissue inflammation and pain Potential use in companion animals"; The Veterinary Journal vol. 173; 2007; pp. 21-30.
E. Roe, et al.; "Fatty Acid Amides"; Notes vol. 74; Jul. 1952; pp. 3442-3443.
S. Luan; "Introducing Immuniphilins from Organ Transplantaion to plant Biology"; Plant Physiology, vol. 134; Apr. 2004; pp. 1241-1243.
D. Sabatini, et al.; "Neural Roles of Immunophilins and Their Ligands"; Molecular Neuobiology vol. 15; 1997; pp. 223-239.
H. Sauer, et al.; "Systemic treatment with GPI 1046 improves spatial memory and reserves cholinergic neuron atrophy in the medial septal nucleus of aged mice"; Brain Research vol. 842; 1999; pp. 109-118.

(56) References Cited

OTHER PUBLICATIONS

C. Sich, et al.; "Solution structure of a neotrophic ligand bound to FKBP12 and its effects on protein dynamics"; European Journal of Biochemistry vol. 267; Feb. 2000; pp. 5342-5354.

J. Steiner, et al.; "Neurotrophic immuniphilin ligands stimulate structural and functional reeovery in neurodegenerative animal models"; Proceedings of the National Academy of Sciences USA vol. 94; Neurobiology; Mar. 1997; pp. 2019-2024.

J. Steiner, et al; "Neurotrophic actions of nonimmunosuppressive analogues of immunosupressive drugs FK506 rapamycin and cyclosporin A"; Nature Medicine vol. 3, No. 4; Nature Publishing Group; Apr. 1997; pp. 421-428.

F. Sun, et al; "Design and Structure-Based Study of New Potential FKBP12 Inhibitors"; Biophysical Journal vol. 85; Nov. 2003; pp. 3194-3201.

G. Sun, et al.; "Carbamazepine and Topiramate Modulation of Transient and Persistent Sodium Currents Studied in HEK293 Cells Expressings the Na 1.3a-Subunit"; Epilepsia vol. 48; Blackwell Publishing, Inc., International League Against Epilepsy; 2007; pp. 774-782.

T. Rhen, et al.; "Antiinflammatory Action of Glucocorticoids—New Mechanism for Old Drugs"; The New England Journal of Medicine vol. 353; Massachusetts Medical Society 2005; pp. 1711-1723.

\* cited by examiner

COMPOSITIONS AND METHODS FOR TREATING INFLAMMATORY DISORDERS

CROSS REFERENCE TO RELATED APPLICATIONS

This application is a 35 U.S.C. §371 National Phase Entry Application from PCT/IL2009/000739, filed Jul. 29, 2009, and designating the United States, which claims the benefit of U.S. Provisional Patent Application No. 61/085,008, filed on Jul. 31, 2008 and the benefit of U.S. Provisional Patent Application No. 61/098,802, filed on Sep. 22, 2008, which are incorporated herein in their entireties.

FIELD AND BACKGROUND OF THE INVENTION

The present invention relates to compositions suitable for treatment of inflammatory disorders and to methods utilizing same in treatment of inflammatory disorders such as cutaneous inflammatory diseases.

Inflammation occurs when tissues are injured by viruses, bacteria, trauma, chemicals, heat, cold or any other harmful stimulus. Chemicals including bradykinin, histamine, serotonin and others are released, attracting tissue macrophages and white blood cells to localize in an area to engulf and destroy foreign substances. During this process, chemical mediators such as TNFα are released, giving rise to inflammation. Inflammatory disorders are those in which the inflammation is sustained or chronic. One example of an inflammatory disorder is osteoarthritis.

Local inflammatory diseases include, for example, asthma, oral mucosal, gastrointestinal inflammation, ocular, nasal and aural inflammation and other steroid responsive inflammatory disorders and conditions. Cutaneous inflammatory diseases include for example, psoriasis, atopic dermatitis, scleroderma and other steroid responsive cutaneous inflammatory disorders conditions such as uremic pruritus and skin conditions associated with exposure to radiation and chemotherapy as well as exposure to environmental radiation and irritants.

Topical steroids have been used in the treatment of inflammatory disorders, as described in U.S. Pat. No. 3,934,013 to Poulsen and references cited therein. Typically, moderate to severe cases of psoriasis require use of a mid-potency steroid such as mometasone furoate (Elocon™) or even a high-potency steroid such as halobetasol (Ultravate™). Topical application of glucocorticoids may suppress the body's own production of cortisol by the adrenal glands, however, especially in the case of relatively high potent products. Accordingly, compositions for treating inflammatory disorders without utilizing mid-potency or high-potency steroids or with use of substantially reduced steroid concentrations would be very useful.

Palmitoylethanolamine (PEA), a member of the class of compounds known as N-acylethanolamines (NAEs), was discovered in 1957 by Kuehl et al (The Identification of N-(2-hydrooxytheyl)-palmitamide as a naturally occurring anti-inflammatory agent, J Am Chem Soc 1957, 79:5577).

PEA, or N-(2-hydroxyethyl)hexadecanamide (also known as palmitoylethanolamide or palmidrol), is a naturally occurring C16:0 fatty acid derivative wherein the carboxylate function is amidated by the primary amine of ethanolamine. N-acylethanolamine compounds are known to have anti-inflammatory and anti-nociceptive effects, as described in Lambert et al (Lambert D M, Vandevoorde S, Jonsson K O, Fowler C J. Curr Med Chem. 2002; 9:663-74); Lambert D M et al (Lambert D M, DiPaolo F G, Sonveaux P, Kanyonyo M, Govaerts S J, Hermans E, Bueb J, Delzenne N M, Tschirhart E J. Biochim Biophys Acta. 1999; 1440:266-74); Brown A J (Br J Pharmacol. 2007; 152(5):567-75); and U.S. Pat. No. 5,506,224 and United States patent application 2005/0054730. None of the above references discloses or suggests use of such compounds in combination with corticosteroids and the use thereof in treating inflammatory diseases or disorders.

Tri-cyclic antidepressants, described inter alia in U.S. Pat. Nos. 2,554,736, 3,438,981, 3,420,851, 3,534,041, 3,505,321, 4,013,639, 4,105,785, 6,368,814, have been used for years as anti-depression agents. Topical 5% doxepin hydrochloride (Zonalon™) cream is also used for treatment of moderate pruritus in adult patients with atopic dermatitis or lichen simplex chronicus. U.S. Pat. No. 7,335,371, assigned to CombinatoRx, discloses compositions formulated for topical administration, comprising as the sole active ingredients a tricyclic antidepressant and a corticosteroid, and their use in treating inflammatory disorders. This patent neither discloses nor suggests in any way the ability of compositions of the present invention to utilize a low-potency steroid in therapeutic situations wherein a mid-potency or high-potency steroid would otherwise be required; or to utilize a mid-potency steroid wherein a high-potency steroid would otherwise be required.

Sulfonamide-class carbonic anhydrase inhibitors such as sulfamate-substituted monosaccharides, of which topiramate is an example, have been long used as anti-convulsive compounds. Topical formulations containing such compounds are proposed for use in treatment of glaucoma and in the assessment of corneal function, as described in U.S. Pat. Nos. 5,059,613 and 5,242,937, and for eczema, as described in WO2007/067036. None of the above references discloses or suggests use of such compounds in combination with corticosteroids and their use in treating cutaneous inflammatory diseases and disorders.

Monoamine oxidase inhibitors (MAOI) and used as antidepressive treatments and are described inter alia in U.S. Pat. Nos. 5,508,311, 5,792,799, 6,472,423, and 6,569,470. None of the above references discloses or suggests use of such compounds in combination with corticosteroids and their use in treating cutaneous inflammatory diseases or disorders.

Cannabinoids are described inter alia in U.S. Pat. Nos. 5,747,524, 5,596,106, 6,017,919, 6,432,984, 6,509,367, 6,645,985, and 7,169,942. Use of such compounds for treating psoriasis has been suggested (Namazi M R. J Eur Acad Dermatol Venereol. 2005 May; 19(3):319-22). None of the above references discloses or suggests use of such compounds in combination with corticosteroids and the use thereof in treating cutaneous inflammatory diseases or disorders.

While reducing the present invention to practice, the present inventors have uncovered that combined use of corticosteroids and PEA, as well as other compounds produces unexpected results in treatment of inflammatory disorders and that PEA has the potential to augment the therapeutic properties of steroids—including increasing therapeutic activity as well as reducing steroid associated adverse effects.

SUMMARY OF THE INVENTION

According to one aspect of the present invention there is provided a composition-of-matter comprising an N-acylethanolamine compound and a corticosteroid.

According to further features in preferred embodiments of the invention described below, the N-acylethanolamine compound is N-palmitoylethanolamine.

According to still further features in the described preferred embodiments the corticosteroid is a low potency corticosteroid.

According to still further features in the described preferred embodiments the composition-of-matter of claim 1 and a pharmaceutically acceptable carrier.

According to still further features in the described preferred embodiments the pharmaceutically acceptable carrier is suitable for topical administration.

According to still further features in the described preferred embodiments the pharmaceutically acceptable carrier is suitable for mucosal administration.

According to still further features in the described preferred embodiments the pharmaceutically acceptable carrier is suitable for oral administration.

According to still further features in the described preferred embodiments the N-acylethanolamine compound is N-palmitoylethanolamine.

According to still further features in the described preferred embodiments the corticosteroid is hydrocortisone.

According to another aspect of the present invention there is provided a medical device comprising the composition-of-matter described herein.

According to still further features in the described preferred embodiments the composition-of-matter forms a coating of the medical device.

According to still another aspect of the present invention there is provided a method for treating an inflammatory disorder comprising administering to a subject in need thereof a composition comprising an N-acylethanolamine compound and a corticosteroid, thereby treating the inflammatory disorder.

According to still further features in the described preferred embodiments the N-acylethanolamine compound is N-palmitoylethanolamine.

According to still further features in the described preferred embodiments the corticosteroid is a low-potency corticosteroid.

According to still further features in the described preferred embodiments the corticosteroid is hydrocortisone.

According to still further features in the described preferred embodiments the inflammatory disorder is caused by a cutaneous inflammatory disease or disorder and the administering is effected via topical delivery.

According to still further features in the described preferred embodiments the cutaneous inflammatory disease is selected from the group consisting of psoriasis, atopic dermatitis and scleroderma.

According to still further features in the described preferred embodiments the inflammatory disorder is caused by asthma and the administering is effected via inhalation.

According to still further features in the described preferred embodiments the inflammatory disorder is caused by gastrointestinal inflammation.

According to still further features in the described preferred embodiments the inflammatory disorder is caused by ocular inflammation.

According to still another aspect of the present invention there is provided a composition-of-matter comprising a corticosteroid and a tricyclic antidepressant.

According to still further features in the described preferred embodiments the tricyclic antidepressant is selected from the group consisting of amitriptyline, maprotiline, clomipramine, desipramine, imipramine, trimipramine, nortriptyline, and protriptyline According to yet another aspect of the present invention there is provided a composition-of-matter comprising a GABA agonist and a corticosteroid.

According to still further features in the described preferred embodiments the GABA agonist is selected from the group consisting of topiramate, muscimol, progabide, riluzole, baclofen, gabapentin, vigabatrin, valproic acid, tiagabine, lamotrigine, pregabalin, phenyloin, and carbamazepine.

According to yet another aspect of the present invention there is provided a composition-of-matter comprising a monoamine oxidase inhibitor (MAOI), and a corticosteroid.

According to still further features in the described preferred embodiments the monoamine oxidase inhibitor is selected from the group consisting of moclobemide, clorgiline, iproclozide, iproniazid, isocarboxazid, minaprine, nialamide, pargyline, phenelzine, rasagiline, selegiline, toloxatone, tranylcypromine, furazolidone, and procarbazine.

According to still another aspect of the present invention there is provided a composition-of-matter comprising a cannabinoid receptor agonist and a corticosteroid.

According to still further features in the described preferred embodiments the cannabinoid receptor agonist is selected from the group consisting of cannabidiol (CBD), cannabidivarol (CBDV), cannabinol (CBN), cannabigerol (CBG), cannabivarol (CBV), cannabicyclol (CBL), tetrahydrocannabinol (THC), tetrahydrocannabinol-C4, (THC-C4), tetrahydrocannabivarin, 11-Hydroxy-$\Delta^9$-tetrahydrocannabinol, (11-OH-THC), and 11-nor-9-Carboxy-$\Delta$9-tetrahydrocannabinol.

According to still another aspect of the present invention there is provided a composition-of-matter comprising an inhibitor of an immunophilin and a low-potency corticosteroid.

According to still further features in the described preferred embodiments the inhibitor of an immunophilin is selected from the group consisting of FK 1706, GPI 1046, GPI 1485, GM-284, (3R)-4-(p-Toluenesulfonyl)-1,4-thiazane-3-carboxylic acid-L-Leucine ethyl ester and (3R)-4-(p-Toluenesulfonyl)-1,4-(thiazane-3-carboxylic acid-L-phenylalanine benzyl ester.

According to yet another aspect of the present invention there is provided a pharmaceutical composition comprising any of the composition-of-matters described hereinabove and a pharmaceutically acceptable carrier selected for topical delivery.

The present invention successfully addresses the shortcomings of the presently known configurations by providing a composition for treating inflammatory disorder which employs substantially reduced doses of a corticosteroid.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
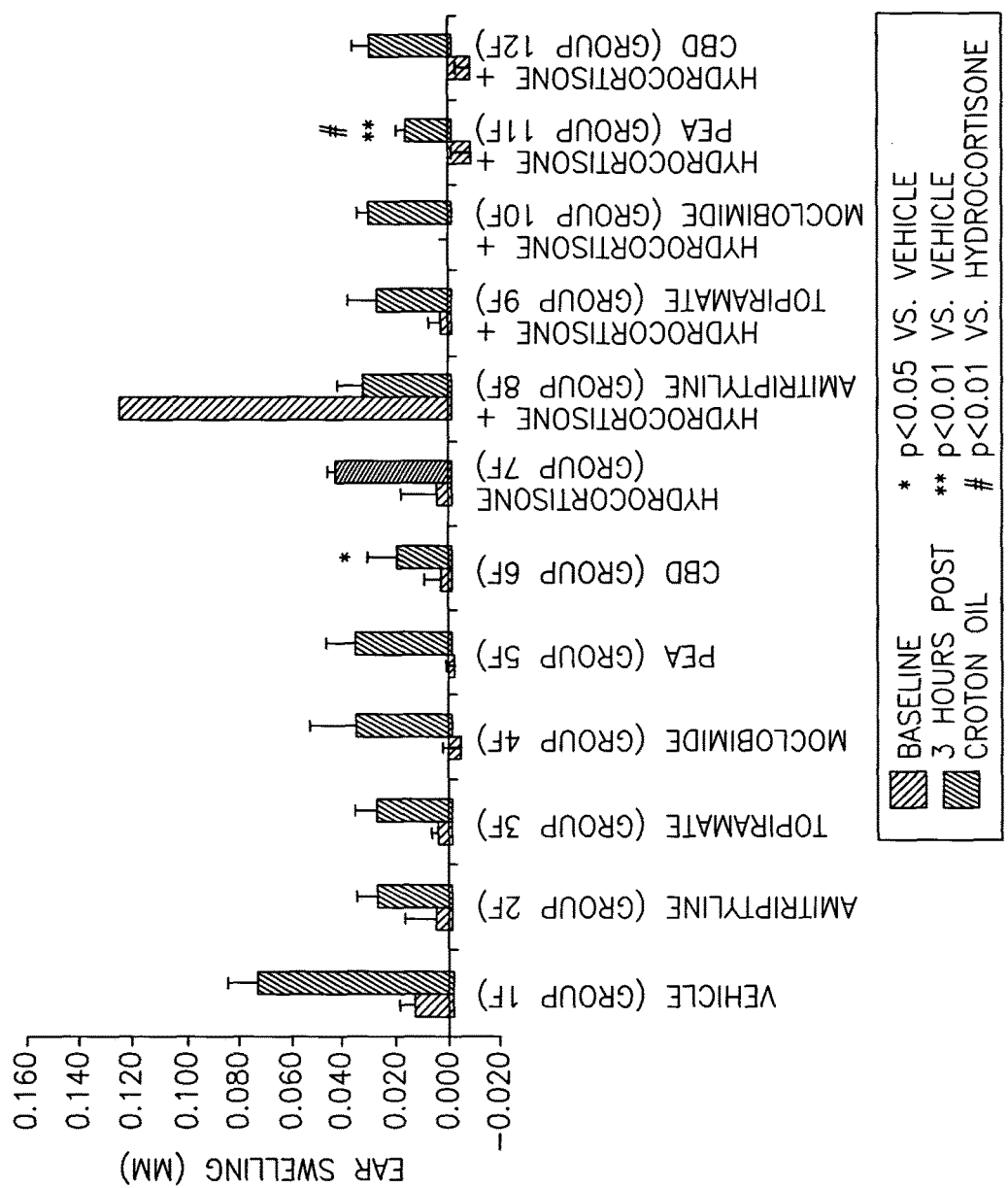
FIG. 1 is a graph representing mean group ear swelling (in mm). Ear thickness was measured prior to (baseline), and 3 hours following, croton oil induced ear sensitization.

The present invention is of compositions which can be used to treat inflammatory disorders.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Inflammatory disorders are typically treated with corticosteroids which can lead to serious side effects which mimic Cushing's disease, a malfunction of the adrenal glands resulting in an overproduction of cortisol. Other potential side effects associated with use of corticosteroids include increased appetite and weight gain, deposits of fat in chest, face, upper back, and stomach and water and salt retention leading to swelling and edema. Thus, there is a great need to decrease the use of corticosteroids in treatment of inflammatory disorders.

The present inventors have devised compositions which include a corticosteroid and a second compound which synergistically complements the corticosteroid in treatment of inflammatory disorders. As a result of this synergism, the present compositions can be used to treat inflammatory disorders with substantially lower concentrations of corticosteroids or with low potency corticosteroids, thereby augmenting the therapeutic properties of steroids by increasing its therapeutic activity and/or reducing steroid associated adverse effects. As a result the present compositions provide a substantial corticosteroid sparing effect.

Thus according to one aspect of the present invention there is provided a composition which includes a corticosteroid and an additional compound selected for complementing the anti-inflammatory effect of the corticosteroid.

According to a presently preferred embodiment of the present invention, the composition of the present invention includes a corticosteroid and an N-acylethanolamine compound such as palmitoylethanolamide (PEA).

N-acylethanolamine compounds are well known in the art, and are described, inter alia, in Lambert et al (Lambert D M, Vandevoorde S, Jonsson K O, Fowler C J. Curr Med Chem. 2002; 9:663-74) and in U.S. Pat. No. 5,506,224 and United States patent application 2005/0054730, which are incorporated by reference herein.

Preferably, the N-acylethanolamine compound of methods and compositions of the present invention is palmitoylethanolamine (PEA)

The N-acylethanolamine compound can also be OEA, Me-PEA or PIA (Jonsson et al, Vandevoorde S, Lambert D M, Tiger G, Fowler C J. Br J Pharmacol. 2001; 133:1263-75):

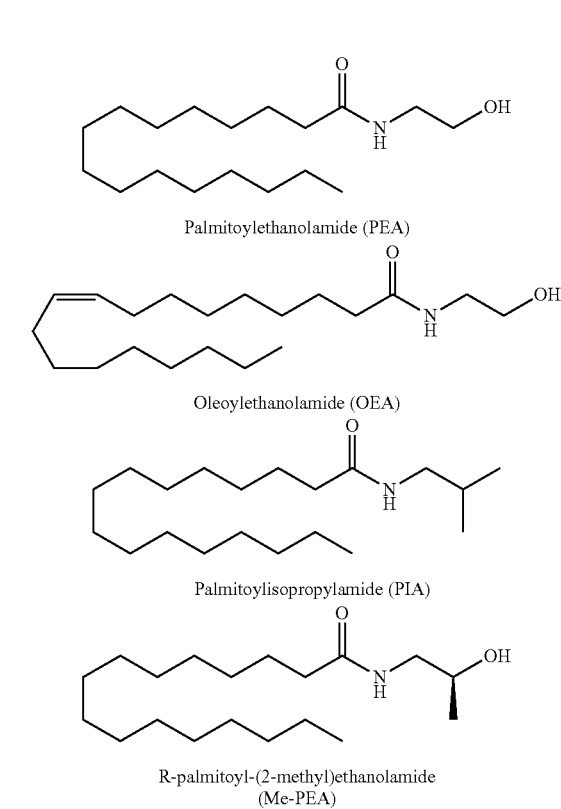

Palmitoylethanolamide (PEA)

Oleoylethanolamide (OEA)

Palmitoylisopropylamide (PIA)

R-palmitoyl-(2-methyl)ethanolamide (Me-PEA)

The N-acylethanolamine compound can have a side chain length of 16 carbon units. Alternatively, the N-acylethanolamine compound can be decanoylethanolamide (C10:0) lauroylethanolamide (C12:0), or myristoylethanolamide (C14:0).

The N-acylethanolamine compound can be an N-15 acylethanolamine derivative. The ethanolamide group of the N-acylethanolamine compound can be replaced with a moiety such as, butylamide, isopro-pylamide, cyclohexamide and (2-methyl)ethanolamide. Each possibility represents a separate embodiment of the present invention.

The N-acylethanolamine compound can be a palmitoylethanolamine derivative. The ethanolamide group of palmitoylethanolamine can be replaced with a moiety such as butylamide, isopropylamide, cyclohexamide and (2-methyl) ethanolamide. The N-acylethanolamine compound can be, for example, palmitoylcyclohexamide, palmitoylbutylamide, palmitoylisopropylamide, palmitoylethanolamide, or Me-palmitoylethanolamide. Each possibility represents a separate embodiment of the present invention.

The N-acylethanolamine compound of the composition of the present invention can be, for example, oleoylethanolamide (OEA) or a derivative thereof. The ethanolamide group of OEA can be replaced with a moiety such as, butylamide, isopro-pylamide, cyclohexamide or (2-methyl) ethanolamide.

OEA, its derivatives, and methods for synthesizing same are well known in the art, and are described, inter alia, in U.S. Pat. Nos. 6,656,972 and 7,348,338 and United States patent application 2002/0173550, which are incorporated herein by reference.

Methods for synthesizing N-acylethanolamine compounds are well known in the art. As described in Lambert et al, PEA was initially synthesized by refluxing ethanolamine with palmitic acid (Roe et al, J Am Chem Soc 1952, 74:3442), yielding white crystals melting at 98-99° C. Due to the simplicity of structure, various syntheses of PEA have been described: the acyl chloride is the most common, but activating agents such as dicyclohexylcarbodiimide and carbonyldiimidazole allow the condensation between the acid and the ethanolamine in very good yields (>80%).

As is described in the Examples section which follows, the present inventors have shown, for the first time, that N-acylethanolamine compounds exhibit a steroid-sparing effect. Such effects enable use of a low-potency steroid in instances wherein a mid-potency or high-potency steroid is typically required or use of lower doses of a high potency steroid, in addition to mitigating steroid associated cutaneous adverse effects. Each possibility represents a separate embodiment of the present invention. Corticosteroid and N-acylethanolamine compounds useful in the invention include those described herein in any of their pharmaceutically acceptable forms, including isomers such as diastereomers and enantiomers, salts, solvates, and polymorphs thereof, as well as racemic mixtures of the compounds described herein.

Corticosteroids that form a part of the present composition include low to very high potency corticosteroids.

Non-limiting examples of low-potency topical corticosteroids include hydrocortisone (available as 0.5% and 1% cream under the names Cortate®, Unicort®, and Cortisporin®).

Nonlimiting examples of mid-potency topical corticosteroids include betamethasone valerate, (available as 0.05% and 0.1% cream under the names Betnovate® and Celestoderm®), clobetasone-17-butyrate (available as 0.05% cream under the name Eumovate®), Flucinonide (available as 0.05% and 0.01% cream under the names 15 Lidex® and Lidemol®), fluocinolone acetonide (available as 0.025% and 0.01% cream under the names Synalar®, Synamol®, and Derma-Smooth®), and triamcinolone acetonide (available as 0.025% and 0.1% cream under the names Aristocort D®, Aristocort R®, Kenalog®, and Vicoderm-KC®).

Non-limiting examples of high-25 potency topical corticosteroids include betamethasone-17-benzoate (available as a 0.025% cream under the name Beben®), betamethasone dipropionate (available as a 0.025% cream under the name Propaderm® and as a 0.05% cream under the names Diprosone® and Diprolene Glycol®), halcinonide (available as a 0.1% cream under the name Halog®), and triamcinolone acetonide (available as a 0.5% cream under the name 30 Aristocort C®).

A non-limiting example of a very-high-potency topical corticosteroid is clobetasol-17-propionate (available as a 0.05% cream under the name Dermovate®). The corticosteroid of the compositions of the present invention can exhibit glucocorticoid activity and/or mineralocorticoid activity. The corticosteroid can be, for example, mometasone and a salt thereof, hydrocortisone, hydrocortisone acetate, hydrocortisone butyrate, hydrocortisone sodium phosphate, hydrocortisone sodium succinate, hydrocortisone cypionate, hydrocortisone probutate, and hydrocortisone valerate.

The corticosteroid can also be, for example, dexamethasone, betamethasone, triamcinolone, triamcinolone acetonide, triamcinolone diacetate, triamcinolone hexacetonide, beclomethasone, dipropionate, beclomethasone dipropionate monohydrate, flumethasone pivalate, diflorasone diacetate, fluocinolone acetonide, fluorometholone, fluorometholone acetate, clobetasol propionate, desoximethasone, fluoxymesterone, fluprednisolone, cortisone acetate, paramethasone 25 acetate, methylprednisolone, methylprednisolone acetate, methylprednisolone sodium succinate, prednisolone, prednisolone acetate, prednisolone sodium phosphate, prednisolone tebutate, clocortolone pivalate, flucinolone, dexamethasone 21-acetate, betamethasone 17-valerate, isoflupredone, 9-fluorocortisone, 6-hydroxydexamethasone, dichlorisone, meclorisone, flupredidene, doxibetasol, halopredone, halometasone, 30 clobetasone, diflucortolone, isoflupredone acetate, fluorohydroxyandrostenedione, beclomethasone, flumethasone, diflorasone, fluocinolone, clobetasol, cortisone, paramethasone, clocortolone, prednisolone 21-hemisuccinate free acid, prednisolone metasulphobenzoate, prednisolone terbutate, and triamcinolone acetonide 21-palmitate.

The corticosteroid can be any naturally occurring or synthetic steroid hormone that can be chemically derived from cholesterol and is characterized by a hydrogenated cyclopentanoperhydrophenanthrene ring system. Naturally occurring corticosteriods are typically generally produced by the adrenal cortex. Synthetic corticosteriods may be halogenated. Functional groups required for activity include a double bond at a C3 ketone, and a C20 ketone.

The compositions of the present invention can be formulated into a pharmaceutical composition.

As used herein, a "pharmaceutical composition" refers to a preparation of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered composition. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include topical, oral, rectal, transmucosal, especially transnasal, intestinal, or parenteral delivery, including intramuscular, subcutaneous, and intramedullary injections, as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For topical, the active ingredients of the pharmaceutical composition may be formulated in crèmes, ointments, solutions, patches, sprays, lotions, liniments, varnishes, solid preparations such as silicone sheets, and the like.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethyl-cellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner or in adhesive carriers.

For administration by inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

The present compositions can also be delivered using an in-situ formed depot (ISFD). Examples of in-situ formed depots include semi-solid polymers which can be injected as a melt and form a depot upon cooling to body temperature. The requirements for such ISFD include low melting or glass transition temperatures in the range of 25-658 C and an intrinsic viscosity in the range of 0.05-0.8 dl/g [12-14]. Below the viscosity threshold of 0.05 dl/g no delayed diffusion could be observed, whereas above 0.8 dl/g the ISFD was no longer injectable using a needle. At injection temperatures above 378 C but below 658 C these polymers behave like viscous fluids which solidify to highly viscous depots. Drugs are incorporated into the molten polymer by mixing without the application of solvents. Thermoplastic pastes (TP) can be used to generate a subcutaneous drug reservoir from which diffusion occurs into the systemic circulation.

In situ cross-linked polymer systems utilize a cross-linked polymer network to control the diffusion of macromolecules over a prolonged period of time. Use of in situ cross-linking implants necessitate protection of the bioactive agents during the cross-linking reaction. This could be achieved by encapsulation into fast degrading gelatin microparticles.

An ISFD can also be based on polymer precipitation. A water-insoluble and biodegradable polymer is dissolved in a biocompatible organic solvent to which a drug is added forming a solution or suspension after mixing. When this formulation is injected into the body the water miscible organic solvent dissipates and water penetrates into the organic phase. This leads to phase separation and precipitation of the polymer forming a depot at the site of injection. One example of such a system is Atrigele™ (ARTIX Laboratories).

Thermally induced gelling systems can also be used as ISFDs. Numerous polymers show abrupt changes in solubility as a function of environmental temperature. The prototype of a thermosensitive polymer is poly(N-isopropyl acryl amide), poly-NIPAAM, which exhibits a rather sharp lower critical solution temperature.

Thermoplastic pastes such as the new generation of poly(ortho esters) developed by AP Pharma can also be used for depot drug delivery. Such pastes include polymers that are semi-solid at room temperature, hence heating for drug incorporation and injection is no longer necessary. Injection is possible through needles no larger than 22 gauge. The drug can be mixed into the systems in a dry and, therefore, stabilized state. Shrinkage or swelling upon injection is thought to be marginal and, therefore, the initial drug burst is expected to be lower than in the other types of ISFD. An additional advantage is afforded by the self-catalyzed degradation by surface erosion.

The compositions of the present invention can also be delivered from medical devices, such as orthopedic implants, contact lenses, micro needle arrays, patches and the like.

Sustained-release (SR), extended-release (ER, XR, or XL), time-release or timed-release, controlled-release (CR), or continuous-release (CR or Contin) pills are tablets or capsules formulated to dissolve slowly and release a drug over time. Sustained-release tablets are formulated so that the active ingredient is embedded in a matrix of insoluble substance (e.g. acrylics, polysaccharides etc) such that the dissolving drug diffuses out through the holes in the matrix. In some SR formulations the matrix physically swells up to form a gel, so that the drug has first to dissolve in matrix, then exit through the outer surface. Difference between controlled release and sustained release is that controlled release is perfectly zero order release that is, the drug releases with time irrespective of concentration. On the other hand, sustained release implies slow release of the drug over a time period. It may or may not be controlled release.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

The dosage of each compound of the claimed combinations depends on several factors, including: the administration method, the disease to be treated, the severity of the disease, whether the disease is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect dosage used.

Continuous daily dosing may not be required; a therapeutic regimen may require cycles, during which time a drug is not administered, or therapy may be provided on an as needed basis during periods of acute inflammation.

Dosages for PEA and various steroids for topical application are exemplified below.
Topical Steroid Group I
PEA (0.3-5%)+Clobetasol diproprionate (0.01-0.05%)
PEA (0.3-5%)+Betamethasone diprorionate 0.05-0.25%
PEA (0.3-5%)+Halbetasol proprionate 0.01-0.05%
PEA (0.3-5%)+Diflorasone diacetate 0.01-0.05%
Topical Steroid Group II
PEA (0.3-5%)+Fluocinonide (0.01 0.05%)
PEA (0.3-5%)+Halcinonide (0.01-0.05%)
PEA (0.3-5%)+Amcinonide (0.01 0.05%)
PEA (0.3-5%)+Desoximetasone (0.05-0.25%)
Topical Steroid Group III
PEA (0.3-5%)+Triamcinalone acetonide (0.01-0.5%)
PEA (0.3-5%)+Mometasone furoate (0.02-0.1%)
PEA (0.3-5%)+Fluticasone proprionate (0.001-0.005%)
PEA (0.3-5%)+Betamethasone diproprionate (0.01-0.05%)
Topical Steroid Group IV
PEA (0.3-5%)+Fluocinolone acetonide (0.05-0.2%)
PEA (0.3-5%)+Hydrocortisone valerate (0.05-0.2%)
PEA (0.3-5%)+Hydrocortisone butyrate (0.02-0.1%)
PEA (0.3-5%)+Flurandrenolide (0.01-0.05%)
PEA (0.3-5%)+Triamcinalone acetonide (0.02-0.1%)
PEA (0.3-5%)+Mometasone furoate (0.02-0.1%)
Topical Steroid Group V
PEA (0.3-5%)+Triamcinalone acetonide (0.02-0.1%)
PEA (0.3-5%)+Fluticasone propionate (0.01-0.05%)
PEA (0.3-5%)+Desonide (0.01-0.05%)
PEA (0.3-5%)+Fluocinolone acetonide (0.005-0.025%)
PEA (0.3-5%)+Hydrocortisone valerate (0.04-0.2%)
Topical Steroid Group VI
PEA (0.3-5%)+Prednicarbate (0.01-0.05%)
PEA (0.3-5%)+Triamcinalone acetonide (0.005-0.025%)
PEA (0.3-5%)+Fluocinolone acetonide (0.002-0.01%)
PEA (0.3-5%)+Desonide (0.01-0.05%)
Topical Steroid Group VII
PEA (0.3-5%)+Hydrocortisone (0.5-2.5%)
PEA (0.3-5%)+Hydrocortisone (0.2-1%)

An Inhalation formulation of a corticosteroid (ICS) and PEA for treatment of, for example, Asthma, COPD and other steroid responsive respiratory diseases and conditions can include a dose of PEA of about 1 microgram to about 500 milligrams per kilogram of the subject, about 100 micrograms to about 200 milligrams per kilogram of the subject, about 100 micrograms to about 5 milligrams per kilogram of the subject, or about 200 micrograms to about 2 milligrams per kilogram of the subject.

The composition can be delivered by dispenser, wherein the dispenser delivers a dose for inhalation of PEA of 1 microgram to about 500 milligrams per kilogram of a subject in need of asthma treatment.

As an inhalant, PEA can be delivered in combination with any of the following steroids:

Beclometasone dipropionate (BDP) 40 to 320 mcg twice daily

Budesonide (BUD) Budesonide 180 to 720 mcg twice daily

Ciclesonide (CIC): 80-320 mcg twice daily.

Fluticasone propionate (FP) 100-500 mcg twice daily.

Mometasone furoate (MF) 220-440 mcg once daily.

A nasal spray formulation of the present composition can include, for example, a dose of PEA of about 1 microgram to about 500 milligrams per kilogram of the subject, about 100 micrograms to about 200 milligrams per kilogram of the subject, about 100 micrograms to about 5 milligrams per kilogram of the subject, or about 200 micrograms to about 2 milligrams per kilogram of the subject.

As a nasal formulation, PEA can be delivered in combination with the following steroids:

Beclomethasone dipropionate, monohydrate, Nasal spay, (84-336 mcg/day).

fluticasone propionate Nasal Spray, (50-200 mcg/day).

Triamcinolone Acetonide (110-220 mcg per day

The present composition can also be formulated for ophthalmic delivery (e.g. as drops) for treatment of ophthalmic diseases.

An ophthalmic formulation of the present composition can include:

PEA (0.3-5%)+loteprednol etabonate ophthalmic suspension, 0.2%);

PEA (0.3-5%)+Betamethasone sodium phosphate (0.05-0.1%); or

PEA (0.3-5%)+Dexamethasone sodium phosphate 0.05-0.1%

Aural preparations of the present invention can include:

PEA (0.3-5%)+Betamethasone sodium phosphate (0.05-0.1%); or

PEA (0.3-5%)+Dexamethasone sodium phosphate 0.05-0.1%

One skilled in the art will be able to ascertain suitable dosages for other steroid compounds for any of the above described formulations.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma or brain levels of the active ingredient to suppress inflammation (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated inflammatory disorder, as further detailed above.

According to another aspect of the present invention there is provided a method of treating an inflammatory disorder. The method is effected by administering to a subject in need a therapeutically effective amount of the present composition. As used herein, the phrase "subject in need" refers to a mammal, preferably a human that is suffering from or is predisposed to an inflammatory disorder.

Local and systemic inflammatory disorders can be treated with the pharmaceutical composition of the present invention. Examples of local inflammatory disorders include, but are not limited to, asthma, gastrointestinal inflammation, ocular inflammation and cutaneous inflammatory disorder. Gastrointestinal inflammation can be caused by gastritis, enteritis, proctitis, inflammatory bowel disease, Crohn disease (CD) or ulcerative colitis (UC). Ocular inflammation can be caused by uvetis or iritis. Cutaneous inflammatory disorder can be caused by psoriasis, atopic dermatitis, and scleroderma.

The present invention also envisages use of a corticosteroid along with a second active agent such as a tricyclic antidepressant, a GABA agonist, a monoamine oxidase inhibitor, a cannabinoid receptor agonist, and an immunophilin inhibitor. The beneficial effects of such second active agent enable use of a low-potency steroid in instances wherein a mid-potency or high-potency steroid is typically required, use of a mid-potency steroid in instances wherein a high-potency steroid is typically required or use of lower doses of a high-potency steroid.

Thus, according to another aspect of the present invention there is provided a composition-of-matter which includes a corticosteroid and at least one additional active ingredient selected form the group consisting of a tricyclic antidepressant, a GABA agonist, a monoamine oxidase inhibitor, a cannabinoid receptor agonist, and an immunophilin inhibitor.

The tricyclic antidepressant, GABA agonist, monoamine oxidase inhibitor, and cannabinoid receptor agonist compounds useful in the invention include those described hereinunder in any of their pharmaceutically acceptable forms, including isomers such as diastereomers and enantiomers, salts, solvates, and polymorphs thereof, as well as racemic mixtures of the compounds described herein. A corticosteroid suitable for use with this aspect of the present invention is described hereinabove.

Compositions including any of the combinations described above can be formulated as for topical administration for treatment of a cutaneous inflammatory disorder that otherwise (in the absence of the tricyclic antidepressant) requires a mid-potency steroid or high-potency steroid). In another embodiment, the tricyclic antidepressant and corticosteroid are the sole active ingredients in the composition. In another embodiment, one or more additional active ingredients are present. In another embodiment, the tricyclic antidepressant and corticosteroid are present in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

In another embodiment, the present invention provides a method for treating a cutaneous inflammatory disease or disorder in a subject in need thereof, the method comprising the step of topically administering to the subject a composition comprising a tricyclic antidepressant and a low-potency corticosteroid, thereby treating a cutaneous inflammatory disease or disorder. In another embodiment, the cutaneous inflammatory disease or disorder is a disease or disorder that otherwise (in the absence of the tricyclic antidepressant) requires a mid-potency steroid or high-potency steroid). In another embodiment, a method of the present invention enables use of a mid-potency steroid in situations wherein a high-potency steroid would otherwise be required. In another embodiment, the method is used to alleviate a cutaneous inflammatory disease or disorder in a subject in need thereof. In another embodiment, the topical administration is performed at a site afflicted by the inflammatory disorder. In another embodiment, the tricyclic antidepressant and corticosteroid are the sole active ingredients in the composition. In another embodiment, one or more additional active ingredients are present. In another embodiment, the tricyclic antidepressant and corticosteroid are present in the composition in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

The tricyclic antidepressant of methods and compositions of the present invention is, in some preferred embodiments, amitriptyline (available as (Elavil®). Non-limiting examples of tricyclic antidepressants useful in methods and compositions of the present invention are amoxapine, 8-hydroxyamoxapine, 7-hydroxyamoxapine, loxapine, loxapine succinate, loxapine hydrochloride, 8-hydroxyloxapine, doxepin, maprotiline, clomipramine, desipramine, imipramine, trimipramine, nortriptyline, and protriptyline. In another embodiment, the tricyclic antidepressant is any other tricyclic antidepressant known in the art. Tricyclic antidepressants are well known in the art, and are described in, for example, U.S. Pat. Nos. 2,554,736, 3,438,981, 3,420,851, 3,534,041, 3,505,321, 4,013,639, 4,105,785, 6,368,814, which are incorporated herein by reference in their entirety. Each possibility represents a separate embodiment of the present invention.

In another embodiment, "tricyclic antidepressant" refers to a compound having one of the formulas: having one the formulas (I), (II), or (III):

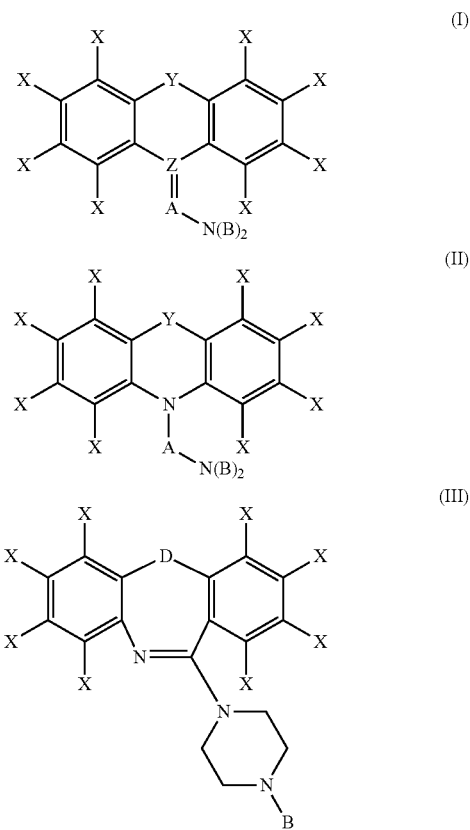

wherein each X is, independently, H, Cl, F, Br, I, $CH_3$, $CF_3$, OH, $OCH_3$, $CH_2CH_3$, or $OCH_2CH_3$; Y is $CH_2$, O, NH, $S(O)_{0-2}$, $(CH_2)_3$, $(CH)_2$, $CH_2O$, $CH_2NH$, CHN, or $CH_2S$; Z is C or S; A is a branched or unbranched, saturated or monounsaturated hydrocarbon chain having between 3 and 6 carbons, inclusive; each B is, independently, H, Cl, F, Br, I, $CX_3$, $CH_2CH_3$, $OCX_3$, or $OCX2CX_3$; and D is $CH_2$, O, NH, $S(O)_{0-2}$.

In another embodiment, each X is, independently, H, Cl, or F; Y is $(CH_2)_2$, Z is C; A is $(CH_2)_3$; and each B is, independently, H, Cl, or F.

In another embodiment of methods and compositions of the present invention, a topical composition comprises an additional active ingredient besides the tricyclic antidepressant and corticosteroid. In another embodiment, more than one additional active ingredients are present. In another embodiment, two additional active ingredients are present. In another embodiment, more than two additional active ingredients are present. Each possibility represents a separate embodiment of the present invention.

In another embodiment, the present invention provides a composition formulated for topical administration, the composition comprising a GABA agonist and a corticosteroid. In another embodiment, the topical administration is in situ topical administration. In another embodiment, the topical administration is in situ topical administration. In another embodiment, the corticosteroid is a low-potency corticosteroid. In another embodiment, the composition is indicated for a cutaneous inflammatory disease or disorder that otherwise (in the absence of the GABA agonist) requires a mid-potency steroid or high-potency steroid). In another embodiment, the GABA agonist and corticosteroid are the sole active ingredients in the composition. In another embodiment, one or more additional active ingredients are present. In another embodiment, the GABA agonist and corticosteroid are present in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

In another embodiment, the present invention provides a method for treating a cutaneous inflammatory disease or disorder in a subject in need thereof, the method comprising the step of topically administering to the subject a composition comprising a GABA agonist and a corticosteroid, thereby treating a cutaneous inflammatory disease or disorder. In another embodiment, the method is used to alleviate a cutaneous inflammatory disease or disorder in a subject in need thereof. In another embodiment, the topical administration is in situ topical administration. In another embodiment, the corticosteroid is a low-potency corticosteroid. In another embodiment, the cutaneous inflammatory disease or disorder is a disease or disorder that otherwise (in the absence of the GABA agonist) requires a mid-potency steroid or high-potency steroid). In another embodiment, the topical administration is performed at a site afflicted by the inflammatory disorder. In another embodiment, the GABA agonist and corticosteroid are the sole active ingredients in the composition. In another embodiment, one or more additional active ingredients are present. In another embodiment, the GABA agonist and corticosteroid are present in the composition in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

In another embodiment of methods and compositions of the present invention, a topical composition comprises an additional active ingredient besides the GABA agonist and corticosteroid. In another embodiment, more than one additional active ingredients are present. In another embodiment, two additional active ingredients are present. In another embodiment, more than two additional active ingredients are present. Each possibility represents a separate embodiment of the present invention.

"GABA agonist" refers, in another embodiment, to an activator of a GABA-gated chloride channel. In another embodiment, the GABA agonist of methods and compositions of the present invention is, in some preferred embodiments, topiramate. Non-limiting examples of GABA agonists useful in methods and compositions of the present invention are topiramate, muscimol, progabide, riluzole, baclofen, gabapentin, vigabatrin, valproic acid, tiagabine, lamotrigine, pregabalin, phenyloin, and carbamazepine. In another embodiment, the GABA agonist is any other GABA agonist known in the art. GABA agonists are well known in the art, and are described, for example, in U.S. Pat. Nos. 5,006,560, 5,248,678, 6,077,839, 6,720,348, and 6,821,985, which are incorporated herein by reference in their entirety. Each possibility represents a separate embodiment of the present invention.

In another embodiment, the present invention provides a composition formulated for topical administration, the composition comprising a carbonic anhydrase inhibitor and a corticosteroid. In another embodiment, the corticosteroid is a low-potency corticosteroid. In another embodiment, the cutaneous inflammatory disease or disorder is a disease or disorder that otherwise (in the absence of the carbonic anhydrase inhibitor) requires a mid-potency steroid or high-potency steroid). In another embodiment, a method of the present invention enables use of a mid-potency steroid in situations wherein a high-potency steroid would otherwise be required. In another embodiment, the topical administration is in situ topical administration. In another embodiment, the carbonic anhydrase inhibitor and corticosteroid are the sole active ingredients in the composition. In another embodiment, one or more additional active ingredients are present. In another embodiment, the carbonic anhydrase inhibitor and corticosteroid are present in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

In another embodiment, the present invention provides a method for treating a cutaneous inflammatory disease or disorder in a subject in need thereof, the method comprising the step of topically administering to the subject a composition comprising a carbonic anhydrase inhibitor and a corticosteroid, thereby treating a cutaneous inflammatory disease or disorder. In another embodiment, the method is used to alleviate a cutaneous inflammatory disease or disorder in a subject in need thereof. In another embodiment, the topical administration is in situ topical administration. In another embodiment, the corticosteroid is a low-potency corticosteroid. In another embodiment, the cutaneous inflammatory disease or disorder is a disease or disorder that otherwise (in the absence of the carbonic anhydrase inhibitor) requires a mid-potency steroid or high-potency steroid). In another embodiment, the topical administration is performed at a site afflicted by the inflammatory disorder. In another embodiment, the carbonic anhydrase inhibitor and corticosteroid are the sole active ingredients in the composition. In another embodiment, one or more additional active ingredients are present. In another embodiment, the carbonic anhydrase inhibitor and corticosteroid are present in the composition in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

The carbonic anhydrase inhibitor of methods and compositions of the present invention is, in some preferred embodiments, topiramate. In another embodiment, the carbonic anhydrase inhibitor is a sulfonamide-class carbonic anhydrase inhibitor. Non-limiting examples of carbonic anhydrase inhibitors useful in methods and compositions of the present invention are topiramate and those compounds described in U.S. Pat. Nos. 4,929,637, 5,276,025, 5,464,831, 5,473,067, 5,646,142, 7,030,250, 7,109,353, which are incorporated herein by reference in their entirety. In another embodiment, the carbonic anhydrase inhibitor is any other carbonic anhydrase inhibitor known in the art. Carbonic anhydrase inhibitors are well known in the art, and are described, for example, in the above patents. Each possibility represents a separate embodiment of the present invention.

In another embodiment of methods and compositions of the present invention, a topical composition comprises an additional active ingredient besides the carbonic anhydrase inhibitor and corticosteroid. In another embodiment, more than one additional active ingredients are present. In another embodiment, two additional active ingredients are present. In another embodiment, more than two additional active ingredients are present. Each possibility represents a separate embodiment of the present invention.

In another embodiment, the present invention provides a composition formulated for topical administration, the composition comprising a sulfamate-substituted monosaccharide and a corticosteroid. In another embodiment, the topical administration is in situ topical administration. In another embodiment, the corticosteroid is a low-potency corticosteroid. In another embodiment, the composition is indicated for a cutaneous inflammatory disease or disorder that otherwise (in the absence of the sulfamate-substituted monosaccharide) requires a mid-potency steroid or high-potency steroid). In another embodiment, a method of the present invention enables use of a mid-potency steroid in situations wherein a high-potency steroid would otherwise be required. In another embodiment, the sulfamate-substituted monosaccharide and corticosteroid are the sole active ingredients in the composition. In another embodiment, one or more additional active ingredients are present. In another embodiment, the sulfamate-substituted monosaccharide and corticosteroid are present in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

In another embodiment, the present invention provides a method for treating a cutaneous inflammatory disease or disorder in a subject in need thereof, the method comprising the step of topically administering to the subject a composition comprising a sulfamate-substituted monosaccharide and a corticosteroid, thereby treating a cutaneous inflammatory disease or disorder. In another embodiment, the method is used to alleviate a cutaneous inflammatory disease or disorder in a subject in need thereof. In another embodiment, the topical administration is in situ topical administration. In another embodiment, the corticosteroid is a low-potency corticosteroid. In another embodiment, the cutaneous inflammatory disease or disorder is a disease or disorder that otherwise (in the absence of the sulfamate-substituted monosaccharide) requires a mid-potency steroid or high-potency steroid). In another embodiment, the topical administration is performed at a site afflicted by the inflammatory disorder. In another embodiment, the sulfamate-substituted monosaccharide and corticosteroid are the sole active ingredients in the composition. In another embodiment, one or more additional active ingredients are present. In another embodiment, the sulfamate-substituted monosaccharide and corticosteroid are present in the composition in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

In another embodiment of methods and compositions of the present invention, a topical composition comprises an additional active ingredient besides the sulfamate-substituted monosaccharide and corticosteroid. In another embodiment, more than one additional active ingredients are present. In another embodiment, two additional active ingredients are present. In another embodiment, more than two additional active ingredients are present. Each possibility represents a separate embodiment of the present invention.

In another embodiment, the present invention provides a composition formulated for topical administration, the composition comprising a monoamine oxidase inhibitor (MAOI), and a corticosteroid. In another embodiment, the topical administration is in situ topical administration. In another embodiment, the topical administration is in situ topical administration. In another embodiment, the corticosteroid is a low-potency corticosteroid. In another embodiment, the composition is indicated for a cutaneous inflammatory disease or disorder that otherwise (in the absence of the monoamine oxidase inhibitor) requires a mid-potency steroid or high-potency steroid). In another embodiment, the monoamine oxidase inhibitor and corticosteroid are the sole active ingredients in the composition. In another embodiment, one or more additional active ingredients are present. In another embodiment, the monoamine oxidase inhibitor and corticosteroid are present in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

In another embodiment, the present invention provides a method for treating a cutaneous inflammatory disease or disorder in a subject in need thereof, the method comprising the step of topically administering to the subject a composition comprising a monoamine oxidase inhibitor and a corticosteroid, thereby treating a cutaneous inflammatory disease or disorder. In another embodiment, the method is used to alleviate a cutaneous inflammatory disease or disorder in a subject in need thereof. In another embodiment, the topical administration is in situ topical administration. In another embodiment, the corticosteroid is a low-potency corticosteroid. In another embodiment, the cutaneous inflammatory disease or disorder is a disease or disorder that otherwise (in the absence of the monoamine oxidase inhibitor) requires a mid-potency steroid or high-potency steroid). In another embodiment, the topical administration is performed at a site afflicted by the inflammatory disorder. In another embodiment, the monoamine oxidase inhibitor and corticosteroid are the sole active ingredients in the composition. In another embodiment, one or more additional active ingredients are present. In another embodiment, the monoamine oxidase inhibitor and corticosteroid are present in the composition in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

The monoamine oxidase inhibitor of methods and compositions of the present invention is, in some preferred embodiments, moclobemide. In another embodiment, the monoamine oxidase inhibitor is a monoamine oxidase A inhibitor. Non-limiting examples of monoamine oxidase inhibitors useful in methods and compositions of the present invention are clorgiline, iproclozide, iproniazid, isocarboxazid (Marplan), minaprine, nialamide, pargyline, phenelzine (Nardil), rasagiline, selegiline (Eldepryl), toloxatone, tranylcypromine (Parnate), furazolidone (Furoxone), and procarbazine (Matulane). In another embodiment, the monoamine oxidase inhibitor is any other monoamine oxidase inhibitor that increases endogenous concentrations of epinephrine (adrenaline). In another embodiment, the monoamine oxidase inhibitor is any other monoamine oxidase inhibitor that increases endogenous concentrations of norepinephrine (noradrenaline). In another embodiment, the monoamine oxidase inhibitor is any other monoamine oxidase inhibitor that increases endogenous concentrations of dopamine. In another embodiment, the monoamine oxidase inhibitor is any other monoamine oxidase inhibitor that increases endogenous concentrations of serotonin. In another embodiment, the monoamine oxidase inhibitor is any other monoamine oxidase inhibitor known in the art to exhibit monoamine oxidase A inhibitory activity. Monoamine oxidase inhibitors are well known in the art, and are described in, for example, U.S. Pat. Nos. 5,508,311, 5,792,799, 6,472,423, and 6,569,470, which are incorporated herein by reference in their entirety. Each possibility represents a separate embodiment of the present invention. Each possibility represents a separate embodiment of the present invention.

In another embodiment of methods and compositions of the present invention, a topical composition comprises an additional active ingredient besides the monoamine oxidase inhibitor and corticosteroid. In another embodiment, more than one additional active ingredients are present. In another embodiment, two additional active ingredients are present. In another embodiment, more than two additional active ingredients are present. Each possibility represents a separate embodiment of the present invention.

In another embodiment, the present invention provides a composition formulated for topical administration, the composition comprising a reversible inhibitor of monoamine oxidase A (RIMA compound) and a corticosteroid. In another embodiment, the topical administration is in situ topical administration. In another embodiment, the topical administration is in situ topical administration. In another embodiment, the corticosteroid is a low-potency corticosteroid. In another embodiment, the composition is indicated for a cutaneous inflammatory disease or disorder that otherwise (in the absence of the RIMA compound) requires a mid-potency steroid or high-potency steroid). In another embodiment, the monoamine oxidase inhibitor and corticosteroid are the sole active ingredients in the composition. In another embodiment, one or more additional active ingredients are present. In another embodiment, the monoamine oxidase inhibitor and corticosteroid are present in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

In another embodiment, the present invention provides a method for treating a cutaneous inflammatory disease or disorder in a subject in need thereof, the method comprising the step of topically administering to the subject a composition comprising a reversible inhibitor of monoamine oxidase A (RIMA compound) and a corticosteroid, thereby treating a cutaneous inflammatory disease or disorder. In another embodiment, the method is used to alleviate a cutaneous inflammatory disease or disorder in a subject in need thereof. In another embodiment, the topical administration is in situ topical administration. In another embodiment, the corticosteroid is a low-potency corticosteroid. In another embodiment, the cutaneous inflammatory disease or disorder is a disease or disorder that otherwise (in the absence of the RIMA compound) requires a mid-potency steroid or high-potency steroid). In another embodiment, the topical administration is performed at a site afflicted by the inflammatory disorder. In another embodiment, the RIMA compound and corticosteroid are the sole active ingredients in the composition. In another embodiment, one or more additional active ingredients are present. In another embodiment, the RIMA compound and corticosteroid are present in the composition in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

The RIMA compound of methods and compositions of the present invention is, in another embodiment, selected from the group consisting of befloxatone, brofaromine, and cimoxatone. In another embodiment, the RIMA compound is a beta-carboline RIMA compound. In another embodiment, the RIMA compound is harmaline). In another embodiment, the RIMA compound is any other RIMA compound known in the art to exhibit monoamine oxidase A inhibitory activity. Each possibility represents a separate embodiment of the present invention.

In another embodiment of methods and compositions of the present invention, a topical composition comprises an additional active ingredient besides the RIMA compound and corticosteroid. In another embodiment, more than one additional active ingredients are present. In another embodiment, two additional active ingredients are present. In another embodiment, more than two additional active ingredients are present. Each possibility represents a separate embodiment of the present invention.

In another embodiment, the present invention provides a composition formulated for topical administration, the composition comprising a cannabinoid receptor agonist and a corticosteroid. In another embodiment, the topical administration is in situ topical administration. In another embodiment, the topical administration is in situ topical administration. In another embodiment, the topical administration is in situ topical administration. In another embodiment, the corticosteroid is a low-potency corticosteroid. In another embodiment, the composition is indicated for a cutaneous inflammatory disease or disorder that otherwise (in the absence of the cannabinoid receptor agonist) requires a mid-potency steroid or high-potency steroid). In another embodiment, the cannabinoid receptor agonist and corticosteroid are the sole active ingredients in the composition. In another embodiment, one or more additional active ingredients are present. In another embodiment, the cannabinoid receptor agonist and corticosteroid are present in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

In another embodiment, the present invention provides a method for treating a cutaneous inflammatory disease or disorder in a subject in need thereof, the method comprising the step of topically administering to the subject a composition comprising a cannabinoid receptor agonist and a corticosteroid, thereby treating a cutaneous inflammatory disease or disorder. In another embodiment, the method is used to alleviate a cutaneous inflammatory disease or disorder in a subject in need thereof. In another embodiment, the topical administration is in situ topical administration. In another embodiment, the corticosteroid is a low-potency corticosteroid. In another embodiment, the cutaneous inflammatory disease or disorder is a disease or disorder that otherwise (in the absence of the cannabinoid receptor agonist) requires a mid-potency steroid or high-potency steroid). In another embodiment, the topical administration is performed at a site afflicted by the inflammatory disorder. In another embodiment, the cannabinoid receptor agonist and corticosteroid are the sole active ingredients in the composition. In another embodiment, one or more additional active ingredients are present. In another embodiment, the cannabinoid receptor agonist and corticosteroid are present in the composition in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

The cannabinoid receptor agonist of methods and compositions of the present invention is, in some preferred embodiments, cannabidiol (CBD). In another preferred embodiment, the cannabinoid receptor agonist is an endocannaboid compound. Non-limiting examples of cannabinoid receptor agonists useful in methods and compositions of the present invention are cannabidivarol (CBDV), cannabinol (CBN), cannabigerol (CBG), cannabivarol (CBV), cannabicyclol (CBL), tetrahydrocannabinol (THC), tetrahydrocannabinol-C4, (THC-C4), tetrahydrocannabivarin (also known as tetrahydrocannabivarol, THCV, and THV), 11-Hydroxy-$\Delta^9$-tetrahydrocannabinol, (11-OH-THC), 11-nor-9-Carboxy-$\Delta$9-tetrahydrocannabinol (11-COOH-THC, THC-COOH, THC-11-oic acid), arachidonoyl ethanolamide (Anandamide, AEA), 2-arachidonoylglycerol (2-AG), 2-Arachidonyl glyceryl ether (noladin ether), virodhamine, N-arachidonoyl-dopamine (NADA), oleamide, A-41988, ajulemic acid, AM-087, AM-411, AM-855, AM-905, AM-906, AM-919, AM-938, AM-4030, AMG-1, AMG-3, AMG-36, AMG-41, dexanabinol (HU-211), DMHP, dronabinol, HU-210, JWH-051, JWH-133, JWH-139, L-759,633, L-759,656, levonantradol, nabilone, Nabitan, O-806, O-823, O-1057, O-1125, O-1238, O-2545, O-2694, parahexyl, THC-O-acetate, THC-O-phosphate, CP 47,497, CP 55,244, CP 55,940, HU-308, 2-Isopropyl-5-methyl-1-(2,6-dihydroxy-4-nonylphenyl)cyclohex-1-ene, AM-630, AM-1241, JWH-015, JWH-018, JWH-073, JWH-081, JWH-200, L-768,242, pravadoline, WIN 55, 212-2, JWH-030, JWH-147, JWH-307, AM-883, Arachidonyl-2'-chloroethylamide, arachidonylcyclopropylamide, methanandamide, O-585, O-689, O-1812, O-1860, O-1861, BAY 38-7271, BAY 59-3074, JWH-171, and O-2220. Cannabinoid receptor agonists are well known in the art, and are described in, for example, U.S. Pat. Nos. 5,747,524, 5,596, 106, 6,017,919, 6,432,984, 6,509,367, 6,645,985, and 7,169, 942, which are incorporated herein by reference in their entirety. In another embodiment, the cannabinoid receptor agonist is any other agonist of a cannabinoid receptor known in the art. Each possibility represents a separate embodiment of the present invention.

In another embodiment, the cannabinoid receptor agonist of methods and compositions of the present invention targets a type 1 (CB1) receptor. In another embodiment, the cannabinoid receptor agonist targets a type 2 (CB2) receptor. In another embodiment, the cannabinoid receptor agonist targets a WIN receptor. In another embodiment, the cannabinoid receptor agonist targets an abnormal-cannabidiol (abn-CBD) receptor. In another embodiment, the cannabinoid receptor agonist targets an anandamide receptor. Each possibility represents a separate embodiment of the present invention.

In another embodiment of methods and compositions of the present invention, a topical composition comprises an additional active ingredient besides the cannabinoid receptor agonist and corticosteroid. In another embodiment, more than one additional active ingredients are present. In another embodiment, two additional active ingredients are present. In another embodiment, more than two additional active ingredients are present. Each possibility represents a separate embodiment of the present invention.

In another embodiment, the present invention provides a composition formulated for topical administration, the composition comprising an immunophilin inhibitor and a corticosteroid. In another embodiment, the topical administration is in situ topical administration. In another embodiment, the topical administration is in situ topical administration. In another embodiment, the topical administration is in situ topical administration. In another embodiment, the corticosteroid is a low-potency corticosteroid. In another embodiment, the composition is indicated for a cutaneous inflammatory disease or disorder that otherwise (in the absence of the immunophilin inhibitor) requires a mid-potency steroid or high-potency steroid). In another embodiment, the immunophilin inhibitor and corticosteroid are the sole active ingredients in the composition. In another embodiment, one or more additional active ingredients are present. In another embodiment, the immunophilin inhibitor and corticosteroid are present in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

In another embodiment, the present invention provides a method for treating a cutaneous inflammatory disease or disorder in a subject in need thereof, the method comprising the step of topically administering to the subject a composition comprising an immunophilin inhibitor and a corticosteroid, thereby treating a cutaneous inflammatory disease or disorder. In another embodiment, the method is used to alleviate a cutaneous inflammatory disease or disorder in a subject in need thereof. In another embodiment, the topical administration is in situ topical administration. In another embodiment, the corticosteroid is a low-potency corticosteroid. In another embodiment, the cutaneous inflammatory disease or disorder is a disease or disorder that otherwise (in the absence of the immunophilin inhibitor) requires a mid-potency steroid or high-potency steroid). In another embodiment, the topical administration is performed at a site afflicted by the inflammatory disorder. In another embodiment, the immunophilin inhibitor and corticosteroid are the sole active ingredients in the composition. In another embodiment, one or more additional active ingredients are present. In another embodiment, the immunophilin inhibitor and corticosteroid are present in the composition in amounts that, when administered together to a patient having cutaneous inflammatory disease or disorder, inhibit or reduce inflammation caused therefrom. In another embodiment, the active ingredients are present in amounts that treat the disorder. Each possibility represents a separate embodiment of the present invention.

In another embodiment of methods and compositions of the present invention, a topical composition comprises an additional active ingredient besides the immunophilin inhibitor and corticosteroid. In another embodiment, more than one additional active ingredients are present. In another embodiment, two additional active ingredients are present. In another embodiment, more than two additional active ingredients are present. Each possibility represents a separate embodiment of the present invention.

The immunophilin inhibitor of methods and compositions of the present invention is, in another embodiment, a non-immunosuppressive immunophilin inhibitor. Non-immunosuppressive immunophilin inhibitors are well known in the art, and include Astellas Pharmaceuticals' FK 1706; Guildford (now MGI) Pharmaceuticals' GPI 1046 and GPI 1485; 2,2'-(1,3,4-oxadiazole-2,5-diyl)bis[1-(3,3-dimethyl-1,2-dioxopentyl)-pyrrolidine (GM-284); (3R)-4-(p-Toluenesulfonyl)-1,4-thiazane-3-carboxylic acid-L-Leucine ethyl ester; and (3R)-4-(p-Toluenesulfonyl)-(-1,4thiazane-3-carboxylic acid-L-phenylalanine benzyl ester. Additional non-immunosuppressive immunophilin inhibitors are described in Adalsteinsson, H., and T. C. Bruice. 2000. Bioorg. Med. Chem. 8:625-635; Gold B G. Expert Opin Investig Drugs. 2000 October; 9(10):2331-42. PMID: 11060810; Gold, B. G., M. Zeleny-Pooley, M. S. Wang, P. Chaturvedi, and D. M. Armistead. 1997. Exp. Neurol. 147:269-278; Guo, X., V. L. Dawson, and T. M. Dawson. 2001. Eur. J. Neurosci. 13:1683-1693; Sabatini, D. M., M. M. Lai, and S. H. Snyder. 1997. Mol. Neurobiol. 15:223-239; Sauer, H., J. M. Francis, H. Jiang, G. S. Hamilton, and J. P. Steiner. 1999. Brain Res. 842:109-118; Sich, C., S. Improta, D. J. Cowley, C. Guenet, J. P. Merly, M. Teufel, and V. Saudek. 2000. Eur. J. Biochem. 267:5342-5355; Steiner, J. P., M. A. Connolly, H. L. Valentine, G. S Hamilton, T. M. Dawson, L. Hester, and S. H. Snyder. 1997. Nat. Med. 4:412-428. Additional non-immunosuppressive immunophilin inhibitors are described in U.S. Pat. Nos. 7,153,883, 6,486,151, 6,331,537, 6,054,452, and 5,846,979 and U.S. Patent application numbers 2003/0186961, 2002/0198250, and 2001/0034362, which are incorporated herein by reference.

In another embodiment, the immunophilin inhibitor is any other immunophilin inhibitor known in the art. Non-limiting examples of immunophilin inhibitors are cyclophilin, FK506 binding protein (FKBP), rapamycin, and analogues thereof. Each immunophilin inhibitor represents a separate embodiment of the present invention.

It is expected that during the life of this patent many relevant corticosteroids will be developed and the scope of the term corticosteroid is intended to include all such new technologies a priori.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples. EXAMPLES Reference is now made to the following examples, which together with the above descriptions, illustrate the invention in a non limiting fashion.

EXAMPLES

Reference is now made to the following examples, which together with the above descriptions, illustrate the invention in a non limiting fashion.

Example 1

A study was undertaken in order to evaluate the effect of topical preparations of various test items (TI) and TI combined with Croton oil on ear swelling. Ear thickness was measured before croton oil induced ear swelling and 3 hours post ear edema induction. The various TIs were applied topically 1 hour prior to ear edema sensitization and 2 hours post ear edema sensitization. The difference in ear thickness of the intact ear was subtracted from the ear thickness of the inflamed ear. This value is defined as "ear swelling".

Materials and Methods

Test System

Species/Strain: Mice/Balb/c

Source: Harlan Israel, Ltd.

Age: Young adults, 6-7 weeks of age at study initiation.

Body Weight: Weight variation of animals at the time of treatment initiation did not exceed±15% of the mean weight.

Animals Health: The health status of the animals used in this study was examined on arrival. Only animals in good health were acclimatized to laboratory conditions and were used in the study.

Acclimation: 5 days.

Housing: During acclimation and following dosing, animals were housed within a limited access rodent facility in conventional cages and kept in groups of maximum 10 mice, in polypropylene cages, fitted with solid bottoms and filled with sterile wood shavings as bedding material.

Food and Water: Animals were provided with ad libitum—a commercial sterile rodent diet and free access to sterile drinking water, supplied to each cage via polyethylene bottles with stainless steel sipper tubes. Feed lot analysis of the diet batch used in the study was included in the archives with the study data.

Environment: Automatically controlled environmental conditions were set to maintain temperature at 20-24° C. with a relative humidity (RH) of 30-70%, a 12:12 hour light: dark cycle and 10-30 air changes/hr in the study room. Temperature and RH were monitored daily.

Identification: Animals were given a unique animal identification ear number. This number also appeared on a cage card, visible on the front of each cage. The cage card also contained the study number, and all other relevant details as to treatment group and dose level.

Randomization: Animals were randomly assigned to experimental groups.

Termination: At the end of the study surviving animals were euthanized by Isoflurane.

Test Groups and Dosages

The Experimental groups used in this study are listed in Table 1 below.

TABLE 1 the 12 experimental groups comprising the study

| Group & Gender | Group Size | Test Item | Route | Concentration | Volume (ml) | Regime | Ear Thickness Measurement |
|---|---|---|---|---|---|---|---|
| 1F | 4 | Vehicle | Topical | 0 | 0.1 | 1 hour prior to | 24 hours prior to |
| 2F | 4 | Amitriptyline | | 2 mg/ml | | | |

TABLE 1-continued the 12 experimental groups comprising the study

| Group & Gender | Group Size | Test Item | Route | Concentration | Volume (ml) | Regime | Ear Thickness Measurement |
|---|---|---|---|---|---|---|---|
| 3F | 4 | Topiramate | | 2 mg/ml | | sensitization and 2 hours post sensitization | sensitization and 3 hours post sensitization |
| 4F | 4 | Moclobimide | | 2 mg/ml | | | |
| 5F | 4 | PEA | | 5 mg/ml | | | |
| 6F | 4 | CBD | | 5 mg/ml | | | |
| 7F | 4 | Hydrocortisone | | 600 nmol/ear | | | |
| 8F | 4 | Hydrocortisone + Amitriptyline | | 600 nmol/ear + 2 mg/ml | | | |
| 9F | 4 | Hydrocortisone + Topiramate | | 600 nmol/ear + 2 mg/ml | | | |
| 10F | 5 | Hydrocortisone + Moclobimide | | 600 nmol/ear + 2 mg/ml | | | |
| 11F | 5 | Hydrocortisone + PEA | | 600 nmol/ear + 5 mg/ml | | | |
| 12F | 5 | Hydrocortisone + CBD | | 600 nmol/ear + 5 mg/ml | | | |

Test Procedure 100 mL (50 mL each side) of freshly prepared Croton oil in acetone (2.5% v/v) solution was applied on Left ear on Study Day 0 to induce sensitization. Prior to sensitization animals were anesthetized. Ear thickness was measured 24 hours prior to croton oil sensitization; this measurement served as a baseline. On sensitization day, the animals were anesthetized using Ketamine and Xylazine formulation. Then, the animals were administered with TI topically. One hour later the animals were introduced to croton oil sensitization (50 μL). Two hours post croton oil sensitization the animals were administered with TI again. Three hours post croton oil sensitization the ear thickness of the animals were measured again.

TIs were administered twice, the first dose was 1 hour prior to croton oil sensitization and the second time was 2 hours post croton oil sensitization. All TIs were dissolved in 10% Ethanol and were applied topically on the surface of the sensitized ear.

Observations and Examinations

Determination of individual body weights of animals was made one day before sensitization phase. A single person was responsible for ear thickness measurement throughout the entire study. The ear thickness of both left and right ears was measured using analogue calipers (Instrumentation 0.01 mm L-01) on 2 occasions: 24 hours prior to croton oil sensitization, and 3 hours post croton oil sensitization.

All data are presented in MEAN±SEM. T-test, two tailed, unpaired was applied to all data. P value was considered significant if $p<0.05$.

No abnormalities were observed following the treatment with all test items. Animal #2 from Group 3F died post anesthesia. The death of this animal was not related to the treatment. Animal #4 (Group 7F) was excluded from the study as redness on ear appeared prior to sensitization with Croton oil. The mean body weight of the animals on the day of study initiation was 18.48±0.15 g. Ear thickness was measured before Croton oil induced ear sensitization (baseline) and 3 hours post ear edema induction. Treatment with various TI was applied topically 1 hour prior to sensitization and 2 hours post induction. The difference in ear thickness of the intact ear was subtracted from the ear thickness measured of the inflamed ear. This value was referred to as ear swelling.

Results

As is shown in Table 3 below and in FIG. 1, the ears of the Vehicle treated animals (Group 1F) swelled significantly over baseline. The difference between the inflamed and intact ear thickness was 0.073±0.012 mm. Treatment with the topical preparation containing CBD (Group 6F) resulted in a significant (72%) inhibition in ear edema compared to the Vehicle group (0.020±0.010 p<0.05). Treatment with the topical preparation containing PEA (Group 5F) resulted in a 52% inhibition of ear swelling, which was not statistically significant. Treatment with the Hydrocortisone preparation (Group 7F) inhibited ear swelling by 40% (0.043±0.003 mm) which was not statistically significant compared to the vehicle group.

Treatment with a combination of the topical preparation containing PEA and the preparation containing Hydrocortisone (Group 11F) resulted in 78% inhibition of ear edema (0.016±0.004 p<0.01 vs. Vehicle and p<0.01 vs. Hydrocortisone).

In view of the findings obtained herein it can be concluded that the CBD test preparation resulted in a significant (72%) inhibition in ear edema compared to the vehicle. The PEA test preparation showed increased (52%) but not significant inhibition of ear swelling in comparison to the hydrocortisone group (40%). However, a combination of the PEA test preparation and the Hydrocortisone test preparation demonstrated a significant reduction in ear edema in comparison to the vehicle group and the hydrocortisone group.

TABLE 2

Mean Group Body weight (g)

| Treatment Group# & Gender | MEAN | SEM |
|---|---|---|
| Vehicle Group 1F | 18.48 | 0.22 |
| Amitriptyline Group 2F | 18.05 | 0.41 |
| Topiramate Group 3F | 18.78 | 0.25 |
| Moclobimide Group 4F | 18.78 | 0.86 |
| PEA Group 5F | 18.45 | 0.58 |
| CBD Group 6F | 18.68 | 0.44 |
| Hydrocortisone Group 7F | 18.35 | 0.26 |

TABLE 2-continued

Mean Group Body weight (g)

| Treatment Group# & Gender | MEAN | SEM |
|---|---|---|
| Hydrocortisone + Amitriptyline Group 8F | 18.25 | 0.22 |
| Hydrocortisone + Topiramate Group 9F | 18.20 | 0.45 |
| Hydrocortisone + Moclobimide Group 10F | 18.34 | 0.49 |
| Hydrocortisone + PEA Group 11F | 18.70 | 0.61 |
| Hydrocortisone + CBD Group 12F | 18.70 | 0.76 |

TABLE 3

Mean Group Ear Swelling (mm) and % of Ear Thickness Inhibition (%)

| Treatment Group# & Gender | Baseline | | 3 Hours Post Croton Oil | | % of Ear Thickness Inhibition |
|---|---|---|---|---|---|
| | MEAN | SEM | MEAN | SEM | |
| Vehicle Group 1F | 0.231 | 0.008 | 0.283 | 0.012 | 0 |
| Amitriptyline Group 2F | 0.223 | 0.006 | 0.248* | 0.005 | 62 |
| Topiramate Group 3F | 0.223 | 0.009 | 0.243 | 0.007 | 63 |
| Moclobimide Group 4F | 0.219 | 0.003 | 0.265 | 0.015 | 52 |
| PEA Group 5F | 0.210 | 0.004 | 0.268 | 0.009 | 52 |
| CBD Group 6F | 0.225 | 0.003 | 0.240* | 0.011 | 72 |
| Hydrocortisone Group 7F | 0.230 | 0.007 | 0.243 | 0.009 | 40 |
| Hydrocortisone + Amitriptyline Group 8F | 0.230 | 0.008 | 0.258 | 0.010 | 55 |
| Hydrocortisone + Topiramate Group 9F | 0.230 | 0.007 | 0.265 | 0.010 | 62 |
| Hydrocortisone + Moclobimide Group 10F | 0.218 | 0.003 | 0.240* | 0.007 | 64 |
| Hydrocortisone + PEA Group 11F | 0.216 | 0.002 | 0.230**# | 0.006 | 78 |
| Hydrocortisone + CBD Group 12F | 0.212 | 0.002 | 0.250* | 0.004 | 59 |

*$p < 0.05$ vs. Vehicle;
**$p < 0.01$ vs. Vehicle;
$p < 0.01$ vs. Hydrocortisone Conclusions The ears of the Vehicle treated animals swelled significantly over baseline and the difference between the inflamed and intact ear thickness was 0.073±0.012 mm. Treatment with the topical preparation containing CBD resulted in a significant (72%) inhibition in ear edema compared to the Vehicle group (0.020±0.010 $p<0.05$) Hydrocortisone preparation inhibited ear swelling by 40% (0.043±0.003 mm). Not statistically significant Treatment with PEA 0.5% resulted in a 52% inhibition of ear swelling, which was not statistically significant versus Hydrocortisone or Vehicle (0.035±0.012 mm). Treatment with a combination of Hydrocortisone and the topical preparation containing PEA (Group 11F) resulted in 78% inhibition of ear edema (0.016±0.004 $p<0.01$ vs. Vehicle and $p<0.01$ vs. Hydrocortisone).

Example 2

A study was undertaken in order to evaluate the effect of topical preparations of Hydrocortisone, Betamethasone and PEA at various concentrations (as single agents and in various combinations) on ear edema in mice. Ear thickness was measured before croton oil induced ear swelling and 6 hours post ear edema induction. The preparations were applied topically 1 hour prior to ear edema sensitization.

The difference in ear thickness of the intact ear was subtracted from the ear thickness of the inflamed ear. This value is defined as "ear swelling".

Materials and Methods

Test systems and procedures are as described above in Example 1, the experimental groups are listed in Table 4 below.

TABLE 4 the 14 experimental groups comprising the study

| Group | Group Size | Test Item | Route | Concentration | Volume (ml) | Regime | Ear Thickness Measurement |
|---|---|---|---|---|---|---|---|
| 1F | 10 | 0.5% PEA | Topical | 0.5% | 25 µl per ear | 0.5 hour prior to sensitization | 24 hours prior to sensitization and 6 hours post sensitization |
| 2F | 10 | 1% PEA | Topical | 1% | 25 µl per ear | | |
| 3F | 10 | 5% PEA | Topical | 5% | 25 µl per ear | | |
| 4F | 10 | 0.5% PEA + Hydrocortisone $ED_{50}$ | Topical | 0.5% | 25 µl per ear | | |
| 5F | 10 | 1% PEA + Hydrocortisone $ED_{50}$ | Topical | 1% | 25 µl per ear | | |
| 6F | 10 | 5% PEA + Hydrocortisone $ED_{50}$ | Topical | 5% | 25 µl per ear | | |

TABLE 4-continued the 14 experimental groups comprising the study

| Group | Group Size | Test Item | Route | Concentration | Volume (ml) | Regime | Ear Thickness Measurement |
|---|---|---|---|---|---|---|---|
| 7F | 10 | 0.5% PEA + Betamethasone $ED_{50}$ | Topical | 0.5% | 25 µl per ear | | |
| 8F | 10 | 1% PEA + Betamethasone $ED_{50}$ | Topical | 1% | 25 µl per ear | | |
| 9F | 10 | 5% PEA + Betamethasone $ED_{50}$ | Topical | 5% | 25 µl per ear | | |
| 10F | 10 | Hydrocortisone $ED_{50}$ | Topical | 55 µg/25 µl per ear | 25 µl per ear | | |
| 11F | 10 | Hydrocortisone $ED_{max}$ | Topical | 200 µg/25 µl per ear | 25 µl per ear | | |
| 12F | 10 | Betamethasone ED50 | Topical | 1 µg/25 µl per ear | 25 µl per ear | | |
| 13F | 10 | Betamethasone $ED_{max}$ | Topical | 4 µg/25 µl per ear | 25 µl per ear | | |
| 14F | 10 | Vehicle (100% Ethanol) | Topical | 0 | 25 µl per ear | | |

Results

Figure 2A:
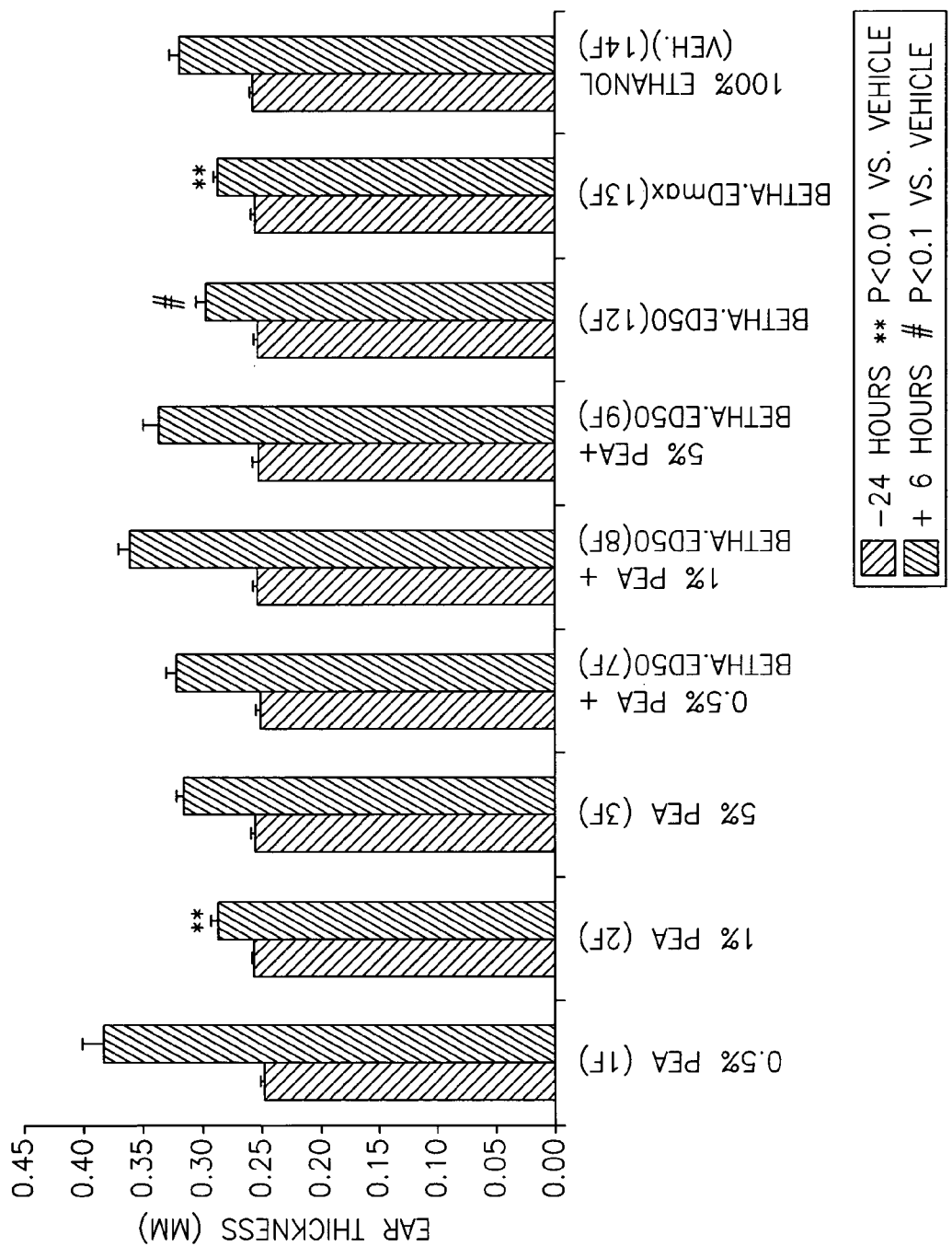
FIG. 2a is a graph representing left Ear thickness (in mm) 6 hours post sensitization. Thickness of sensitized ears was measured 24 hours prior to (baseline), and 6 hours following, croton oil induced ear sensitization
Figure 2B:
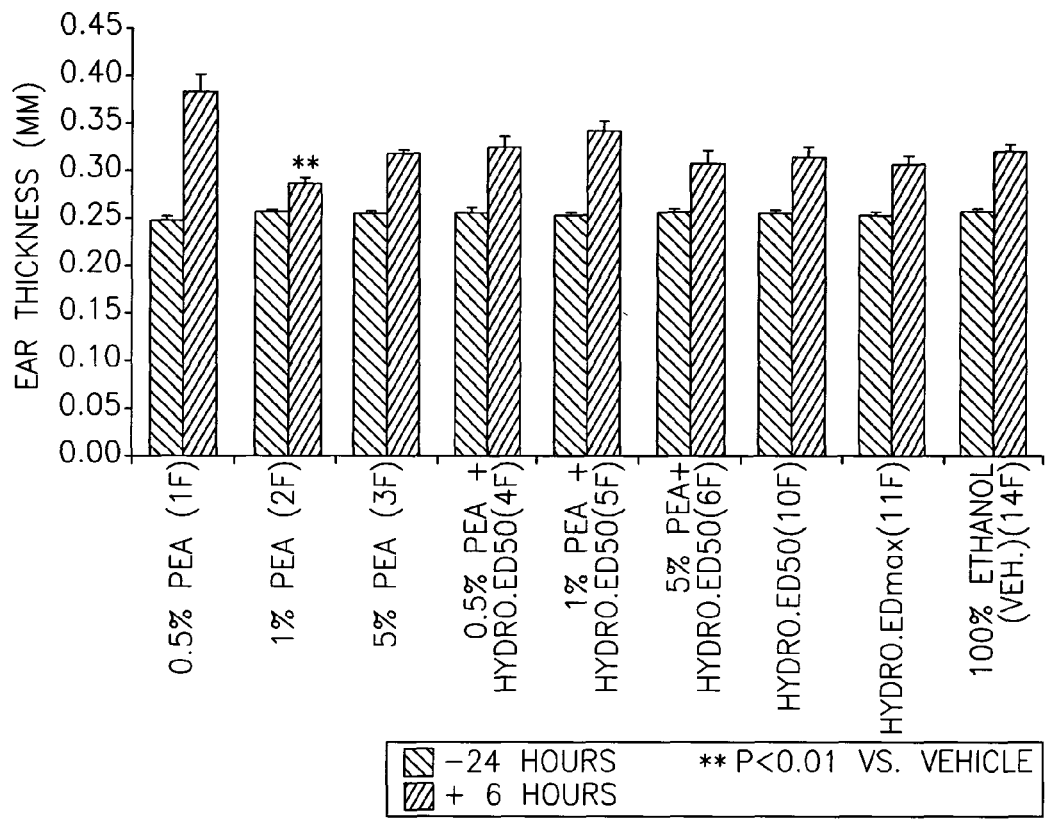
FIG. 2b is a graph representing mean left Ear thickness (in mm) 6 hours post sensitization. Thickness of sensitized ears was measured 24 hours prior to (baseline), and 6 hours following, croton oil induced ear sensitization

Ear Thickness results are listed in Table 6 and illustrated in FIGS. 2a-b); Ear Delta results are listed in Table 7.

Significant ear swelling was measured 6 hours post sensitization in Vehicle treated groups (Group 14F: 0.32±0.01 post sensitization vs. 0.26±0.003 baseline; p<0.01). Treatment with topical preparations of Hydrocortisone at concentrations of 55 µg/25 µl per ear—calculated ($ED_{50}$) and 200 µg/25 µl per ear calculated ($ED_{max}$) was not active compared to vehicle in reducing ear thickness in the current model.

Betamethasone at concentrations of 1 µg/25 µl per ear calculated ($ED_{50}$) and 4 µg/25 µl per ear calculated ($ED_{max}$) demonstrated significant reduction in ear edema compared to vehicle in a dose related manner (Betamethasone at $ED_{50}$ 0.30±0.008, p<0.1; Betamethasone at $ED_{max}$ 0.29±0.005 p<0.05 vs. Vehicle).

Topical preparations of PEA at a concentration of 1% was significantly active in reducing ear thickness by approximately 50% (0.29±0.004, p<0.05 vs. Vehicle). No significant activity was detected for the other preparation groups in this current model.

Thus, topical treatment with PEA (1%) resulted in a significant reduction in ear edema compared to the Vehicle. In addition, treatment with topical preparations of Betamethasone (1 µg/25 µl per ear calculated ($ED_{50}$) and 4 µg/25 µl per ear calculated ($ED_{max}$) demonstrated significant reduction in ear edema compared to vehicle in a dose related manner In view of these results it can be concluded that topical treatment with PEA (1%) results in a significant reduction in ear edema compared to the Vehicle. In addition, this study also demonstrated that treatment with topical preparations of Betamethasone (1 µg/25 µl per ear calculated ($ED_{50}$) and 4 µg/25 µl per ear calculated ($ED_{max}$) lead to significant reduction in ear edema in a dose related manner when compared to vehicle.

TABLE 5

Mean Group Body Weight (g)

| Treatment and Group # | Mean | SEM |
|---|---|---|
| 0.5% PEA(1F) | 18.9 | 0.38 |
| 1% PEA(2F) | 18.4 | 0.35 |
| 5% PEA(3F) | 19.0 | 0.35 |
| 0.5% PEA + Hydro. $ED_{50}$ (4F) | 18.3 | 0.31 |
| 1% PEA + Hydro. $ED_{50}$ (5F) | 18.4 | 0.39 |
| 5% PEA + Hydro. $ED_{50}$ (6F) | 17.6 | 0.32 |
| 0.5% PEA + Beta. $ED_{50}$ (7F) | 18.2 | 0.42 |
| 1% PEA + Beta. $ED_{50}$ (8F) | 18.9 | 0.34 |
| 5% PEA + Beta. $ED_{50}$ (9F) | 18.4 | 0.27 |
| Hydro. $ED_{50}$ (10F) | 17.3 | 0.33 |
| Hydro. $ED_{max}$ (11F) | 18.5 | 0.40 |
| Beta. $ED_{50}$ (12F) | 17.5 | 0.44 |
| Beta. $ED_{max}$ (13F) | 17.6 | 0.40 |
| 100% Ethanol (veh.)(14F) | 18.9 | 0.44 |

TABLE 6

Mean Left Ear Thickness

| | Left Ear Thickness (mm) | | SEM | |
|---|---|---|---|---|
| Treatment and Group # | Study Day −1 (24 H pre sensitization) | Study Day 0 (6 H post sensitization) | Study Day −1 (24 H pre sensitization) | Study Day 0 (6 H post sensitization) |
| 0.5% PEA(1F) | 0.25 | 0.38 | 0.00 | 0.02 |
| 1% PEA(2F) | 0.26 | 0.29 ** | 0.00 | 0.00 |
| 5% PEA(3F) | 0.26 | 0.32 | 0.00 | 0.00 |
| 0.5% PEA + Hydro. $ED_{50}$ (4F) | 0.26 | 0.33 | 0.00 | 0.01 |
| 1% PEA + Hydro. $ED_{50}$ (5F) | 0.25 | 0.34 | 0.00 | 0.01 |

TABLE 6-continued

Mean Left Ear Thickness

| | Left Ear Thickness (mm) | | SEM | |
|---|---|---|---|---|
| Treatment and Group # | Study Day −1 (24 H pre sensitization) | Study Day 0 (6 H post sensitization) | Study Day −1 (24 H pre sensitization) | Study Day 0 (6 H post sensitization) |
| 5% PEA + Hydro. $ED_{50}$ 6F) | 0.26 | 0.31 | 0.00 | 0.01 |
| 0.5% PEA + Beta. $ED_{50}$ (7F) | 0.25 | 0.32 | 0.00 | 0.01 |
| 1% PEA + Beta. $ED_{50}$ (8F) | 0.25 | 0.36 | 0.00 | 0.01 |
| 5% PEA + Beta. (9F) | 0.25 | 0.34 | 0.00 | 0.01 |
| Hydr. $ED_{50}$ (10F) | 0.26 | 0.32 | 0.00 | 0.01 |
| Hydro. $ED_{max}$ (11F) | 0.25 | 0.31 | 0.00 | 0.01 |
| Beta. $ED_{50}$ (12F) | 0.25 | 0.30 * | 0.00 | 0.01 |
| Beta $ED_{max}$ (13F) | 0.26 | 0.29 ** | 0.00 | 0.00 |
| 100% Ethanol (Veh.)(14F) | 0.26 | 0.32 | 0.00 | 0.01 |

* $p < 0.1$ vs. relevant Vehicle;
** $p < 0.01$ vs. relevant Vehicle

TABLE 7

Mean Left Ear Delta thickness

| Hydrocortisone | | | Bethametasone | | |
|---|---|---|---|---|---|
| Treatment/Group # | Delta + 6 h vs baseline | SEM | Treatment/Group # | Delta + 6 h vs baseline | SEM |
| 0.5% PEA(1F) | 0.135 | 0.017 | 0.5% PEA(1F) | 0.135 | 0.017 |
| 1% PEA(2F) | 0.031* | 0.004 | 1% PEA(2F) | 0.031* | 0.004 |
| 5% PEA(3F) | 0.062 | 0.003 | 5% PEA(3F) | 0.062 | 0.003 |
| 0.5% PEA + Hydro. ED50(4F) | 0.068 | 0.012 | 0.5% PEA + Betha. ED50(7F) | 0.070 | 0.008 |
| 1% PEA + Hydro. ED50(5F) | 0.090 | 0.010 | 1% PEA + Betha. ED50(8F) | 0.106 | 0.009 |
| 5% PEA + Hydro. ED50(6F) | 0.051 | 0.013 | 5% PEA + Betha. ED50(9F) | 0.081 | 0.013 |
| Hydro. ED50(10F) | 0.060 | 0.008 | Betha. ED50(12F) | 0.043 | 0.007 |
| Hydro. EDmax(11F) | 0.054 | 0.008 | Betha. EDmax(13F) | 0.031* | 0.004 |
| 100% Ethanol (veh.)(14F) | 0.062 | 0.010 | 100% Ethanol (veh.)(14F) | 0.062 | 0.010 |

*$p < 0.05$ vs. relevant Vehicle

Conclusions

Significant ear swelling was measured 6 hours post sensitization in Vehicle treated groups (Group 14F: 0.32±0.01 post sensitization vs. 0.26±0.003 baseline; p<0.01).

Treatment with topical preparations of Hydrocortisone at concentrations of 55 µg/25 µl per ear—calculated (ED50) and 200 µg/25 µl per ear calculated (EDmax) were not active compared to vehicle in reducing ear thickness in the current model.

Betamethasone at concentrations of 1 µg/25 µl per ear calculated (ED50) and 4 µg/25 µl per ear calculated (EDmax) demonstrated significant reduction in ear edema compared to vehicle in a dose related manner (Betamethasone at ED50 0.30±0.008, p<0.1; Betamethasone at EDmax 0.29±0.005 p<0.05 vs. Vehicle).

Topical PEA at a concentration of 1% was significantly active in reducing ear thickness by approximately 50% (0.29±0.004, p<0.05 vs. Vehicle).

No significant activity was detected for the other preparation groups in this current model.

Example 3

A study was undertaken in order to determine the effect of topical application of a combined preparation of Betamethasone and PEA on ear edema in mice. Ear thickness was measured before croton oil induced ear swelling and 6 and 9 hours post ear edema induction. The preparations were applied topically 1 hour prior to ear edema sensitization.

The difference in ear thickness of the intact ear was subtracted from the ear thickness of the inflamed ear. This value is defined as "ear swelling".

Materials and Methods

Test systems and procedures are as described above in Example 1, the experimental groups are listed in Table 8 below.

TABLE 8 the 4 experimental groups comprising the study

| Group | Group Size | Test Item | Route | Concentration | Volume (ml) Per ear | Regime | Ear Thickness Measurement |
|---|---|---|---|---|---|---|---|
| 1F | 10 | Vehicle (100% Ethanol) | Topical | 0 | 25 µl | 0.5 hour prior to sensitization | 24 hours prior to sensitization |
| 2F | 10 | 1% PEA | Topical | 1% | 25 µl | | |

TABLE 8-continued the 4 experimental groups comprising the study

| Group | Group Size | Test Item | Route | Concentration | Volume (ml) Per ear | Regime | Ear Thickness Measurement |
|---|---|---|---|---|---|---|---|
| 3F | 10 | 1% PEA + Betamethasone $ED_{max}$ | Topical | 1% + 4 µg/25 µl per ear | 25 µl | | and 6 hours post sensitization |
| 4F | 10 | Betamethasone $ED_{max}$ | Topical | 4 µg/25 µl per ear | 25 µl | | |

Results

Figure 3:
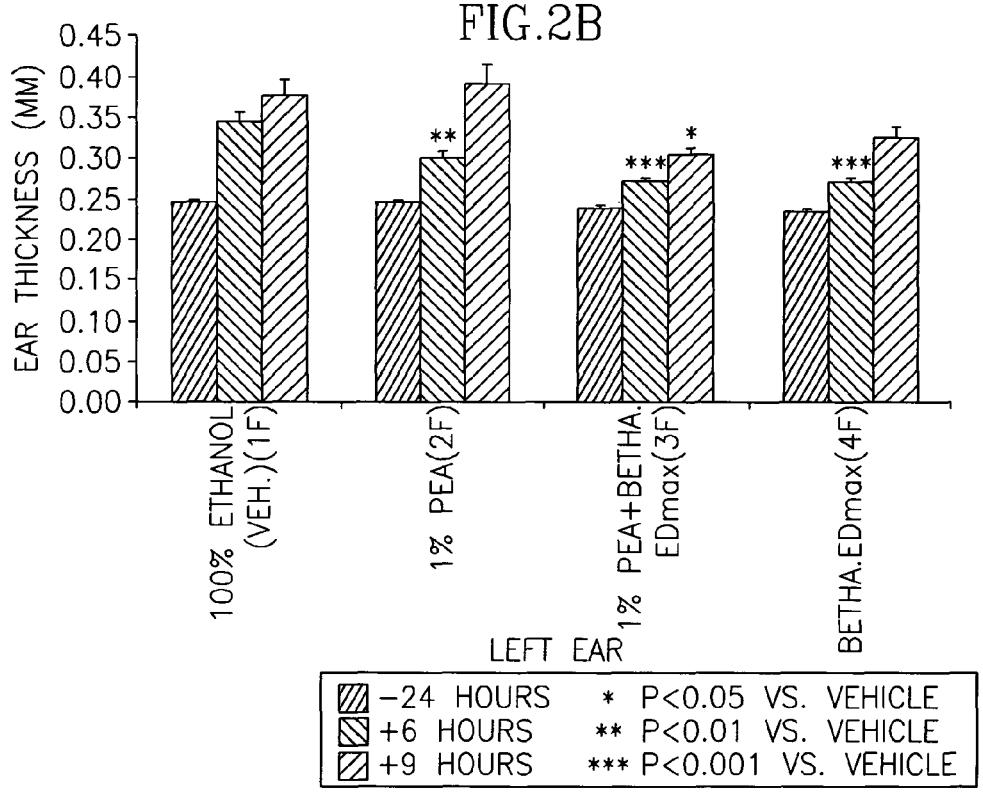
FIG. 3 is a graph representing left ear thickness (in mm) 6 hours and 9 hours post sensitization.

Ear Thickness results are listed in Table 10 and illustrated in FIG. 3; Delta Thickness results are listed in Table 11.

A significant ear swelling was measured 6 hours and 9 hours post sensitization in Vehicle treated group (Group 1F). Ear thickness increased by 0.9 mm 6 hours post sensitization and increased by 0.13 mm 9 hours post sensitization.

PEA 1% preparation (Group 2F) demonstrated significant activity in inhibiting ear swelling 6 hours post sensitization. ($p<0.01$ vs. Vehicle) but was not active in inhibiting ear swelling 9 hours post sensitization.

A single mixture preparation of PEA (1%)+Betamethasone 4 µg/25 µl per ear calculated ($ED_{max}$) (Group 3F) demonstrated significant activity in inhibiting ear swelling 6 hours post sensitization ($p<0.001$ vs. Vehicle) and maintained significant activity at 9 hours post sensitization ($p<0.05$ vs. Vehicle).

Betamethasone 4 µg/25 µl per ear calculated ($ED_{max}$) (Group 4F) was active in inhibiting ear swelling 6 hours post sensitization ($p<0.001$ vs. Vehicle) but was not active at 9 hours post sensitization.

The single mixture preparation of PEA (1%)+Betamethasone 4 µg/25 µl per ear calculated ($ED_{max}$) (Group 3F) was the only preparation that demonstrated significant activity at 9 hours post sensitization ($p<0.05$ vs. Vehicle In view of the above results it can be concluded that a preparation of PEA (1%)+Betamethasone 4 µg/25 µl per ear (Group 3F) demonstrated significant activity in inhibiting ear swelling 6 hours post sensitization and continued to demonstrate significant activity 9 hours post sensitization Topical PEA (1%) preparation (Group 2F) demonstrated significant activity in inhibiting ear swelling 6 hours post sensitization ($p<0.01$ vs. Vehicle) but was not active at 9 hours post sensitization. Betamethasone 4 µg/25 µl per ear calculated ($ED_{max}$) (Group 4F) demonstrated significant activity in inhibiting ear swelling 6 hours post sensitization but was not active at 9 hours post sensitization.

TABLE 9

Mean Group Body Weight (g)

| Treatment and Group # | Mean | SEM |
|---|---|---|
| 100% Ethanol (Veh.) (1F) | 18.16 | 0.42 |
| 1% PEA (2F) | 19.08 | 0.44 |
| 1% PEA + Beta. EDmax (3F) | 18.62 | 0.33 |
| Beta. EDmax(4F) | 18.45 | 0.32 |

TABLE 10

Mean Left Ear Thickness

| | Mean Left Ear Thickness (mm) | | | SEM | | |
|---|---|---|---|---|---|---|
| | | Day 0 | | | Day 0 | |
| Treatment and Group # | Day −1 (24 h pre sensitization) | Day 0 (6 h post sensitization) | (9 h post sensitization) | Day −1 (24 h pre sensitization) | Day 0 (6 h post sensitization) | Day 0 (9 h post sensitization) |
| 100% Ethanol (veh.) (1F) | 0.25 | 0.34 | 0.38 | 0.003 | 0.013 | 0.017 |
| 1% PEA (2F) | 0.25 | 0.30** | 0.39 | 0.003 | 0.008 | 0.024 |
| 1% PEA + Beta.EDmax (3F) | 0.24 | 0.27*** | 0.31* | 0.003 | 0.004 | 0.007 |
| Beta.EDmax (4F) | 0.24 | 0.27*** | 0.33 | 0.003 | 0.006 | 0.012 |

*$p < 0.05$ vs. relevant Vehicle;
**$p < 0.01$ vs. relevant Vehicle;
***$p < 0.001$ vs. relevant Vehicle

TABLE 11

Mean Left Ear Delta Thickness

| Treatment/Group # | Delta + 6 h vs baseline | Delta + 9 h vs baseline | 6 h SEM | 9 h SEM |
|---|---|---|---|---|
| 100% Ethanol (veh.)(1F) | 0.098 | 0.133 | 0.013 | 0.016 |
| 1% PEA(2F) | 0.056* | 0.147 | 0.009 | 0.024 |
| 1% PEA + Beta. EDmax(3F) | 0.032** | 0.066** | 0.005 | 0.006 |
| Beta. EDmax(4F) | 0.036** | 0.092# | 0.005 | 0.011 |

$p < 0.1$,
*$p < 0.05$ vs Vehicle,
**$p < 0.01$ vs Vehicle

Conclusions

Significant ear swelling was measured 6 hours and 9 hours post sensitization in Vehicle treated group. Ear thickness increased by 0.9 mm 6 hours post sensitization and increased by 0.13 mm 9 hours post sensitization.

PEA 1% preparation demonstrated significant activity in inhibiting ear swelling 6 hours post sensitization. ($p<0.01$ vs. Vehicle) but was not active in inhibiting ear swelling 9 hours post sensitization.

Betamethasone 4 μg/25 μl per ear calculated was active in inhibiting ear swelling 6 hours post sensitization ($p<0.001$ vs. Vehicle) but was not active at 9 hours post sensitization.

A single mixture preparation of PEA (1%)+Betamethasone 4 μg/25 μl per ear demonstrated significant activity in inhibiting ear swelling 6 hours post sensitization ($p<0.001$ vs. Vehicle) and maintained significant activity at 9 hours post sensitization ($p<0.05$ vs. Vehicle).

Combination of PEA and Betamethasone prolonged anti-inflammatory activity

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A non-aqueous pharmaceutical composition comprising 0.5% N-palmitoylethanolamine by weight and 600 nmole hydrocortisone and a pharmaceutically acceptable carrier.

2. The pharmaceutical composition of claim 1, wherein said pharmaceutically acceptable carrier is suitable for topical administration.

3. The pharmaceutical composition of claim 1, wherein said pharmaceutically acceptable carrier is suitable for mucosal administration.

4. The pharmaceutical composition of claim 1, wherein said pharmaceutically acceptable carrier is suitable for oral administration.

5. A medical device comprising the pharmaceutical composition of claim 1.

6. The medical device of claim 5, wherein said pharmaceutical composition forms a coating of the medical device.

7. The pharmaceutical composition of claim 1, formulated as a crème, an ointment, a solution, a patch, a spray, a lotion, a liniment, a varnish, or a solid preparation.

* * * * *